(12) United States Patent
Ichikawa

(10) Patent No.: US 11,176,640 B2
(45) Date of Patent: Nov. 16, 2021

(54) ULTRASOUND OBSERVATION DEVICE, METHOD OF OPERATING ULTRASOUND OBSERVATION DEVICE, AND COMPUTER-READABLE RECORDING MEDIUM

(71) Applicant: OLYMPUS CORPORATION, Tokyo (JP)

(72) Inventor: Junichi Ichikawa, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 735 days.

(21) Appl. No.: 16/015,484

(22) Filed: Jun. 22, 2018

(65) Prior Publication Data
US 2018/0308221 A1 Oct. 25, 2018

Related U.S. Application Data

(63) Continuation of application No. PCT/JP2016/087836, filed on Dec. 19, 2016.

(30) Foreign Application Priority Data

Dec. 24, 2015 (JP) .............................. JP2015-252210

(51) Int. Cl.
*G06T 5/00* (2006.01)
*A61B 8/12* (2006.01)
(Continued)

(52) U.S. Cl.
CPC ................ *G06T 5/002* (2013.01); *A61B 8/12* (2013.01); *A61B 8/14* (2013.01); *A61B 8/5238* (2013.01);
(Continued)

(58) Field of Classification Search
CPC ........... G06T 5/002; G06T 2207/10132; G06T 2207/20024; A61B 8/12; A61B 8/14; A61B 8/5238; A61B 8/5269; A61B 8/54
See application file for complete search history.

(56) References Cited

U.S. PATENT DOCUMENTS 9,833,218 B2 * 12/2017 Kho ........................ A61B 8/483
2007/0221850 A1 * 9/2007 Panin ..................... G01T 1/1617
250/363.04

(Continued)

FOREIGN PATENT DOCUMENTS

EP    2 526 870 A1    11/2012
EP    3 155 971 A1    4/2017
(Continued)

OTHER PUBLICATIONS

Extended Supplementary European Search Report dated Jul. 8, 2019 in European Patent Application No. 16 87 8645.7.
(Continued)

*Primary Examiner* — Sanjay Cattungal
(74) *Attorney, Agent, or Firm* — Scully, Scott, Murphy & Presser, P.C.

(57) ABSTRACT

An ultrasound observation device includes a controller. The controller is configured to: calculate feature data of an ultrasound signal by analyzing the ultrasound signal; divide an area of interest preliminarily set on an ultrasound image into a plurality of sections; and set an attenuation rate for each of the sections; correct the attenuation rate in a range including at least a boundary between adjacent sections in a manner smoothly changing across the adjacent sections; and perform attenuation correction on the feature data using the corrected attenuation rate to calculate correction feature data.

16 Claims, 15 Drawing Sheets

(51) Int. Cl.
*A61B 8/14* (2006.01)
*A61B 8/08* (2006.01)
*A61B 8/00* (2006.01)

(52) U.S. Cl.
CPC .............. *A61B 8/5269* (2013.01); *A61B 8/54* (2013.01); *G06T 2207/10132* (2013.01); *G06T 2207/20024* (2013.01)

(56) References Cited

U.S. PATENT DOCUMENTS

| | | | |
|---|---|---|---|
| 2012/0281497 A1 | 11/2012 | Noguchi | |
| 2012/0310087 A1* | 12/2012 | Miyaki | A61B 8/461 600/440 |
| 2013/0012818 A1* | 1/2013 | Miyaki | A61B 8/5269 600/442 |
| 2013/0030296 A1* | 1/2013 | Miyaki | G01S 7/52036 600/442 |
| 2013/0035594 A1* | 2/2013 | Eda | G01S 7/52046 600/442 |
| 2013/0113938 A1* | 5/2013 | Miyaki | A61B 8/5207 348/163 |
| 2014/0163373 A1 | 6/2014 | Noguchi | |
| 2015/0112198 A1* | 4/2015 | Yamamoto | A61B 8/5207 600/447 |
| 2015/0148673 A1* | 5/2015 | Yoshikawa | A61B 8/5207 600/438 |
| 2015/0196280 A1* | 7/2015 | Yamamoto | A61B 8/5269 600/440 |
| 2015/0196283 A1* | 7/2015 | Yamamoto | A61B 8/0825 600/437 |
| 2015/0196284 A1* | 7/2015 | Yamamoto | G10K 11/346 600/447 |
| 2017/0112475 A1 | 4/2017 | Miyaki | |

FOREIGN PATENT DOCUMENTS

| | | |
|---|---|---|
| JP | 2010-246640 A | 11/2010 |
| WO | WO 2013/132717 A1 | 9/2013 |
| WO | 2015/190180 A1 | 12/2015 |
| WO | WO 2016/006288 A1 | 1/2016 |

OTHER PUBLICATIONS

International Search Report dated Mar. 7, 2017 issued in PCT/JP2016/087836.

* cited by examiner

ULTRASOUND OBSERVATION DEVICE, METHOD OF OPERATING ULTRASOUND OBSERVATION DEVICE, AND COMPUTER-READABLE RECORDING MEDIUM

CROSS REFERENCES TO RELATED APPLICATIONS

This application is a continuation of PCT international application Ser. No. PCT/JP2016/087836 filed on Dec. 19, 2016 which designates the United States, incorporated herein by reference, and which claims the benefit of priority from Japanese Patent Applications No. 2015-252210, filed on Dec. 24, 2015, incorporated herein by reference.

BACKGROUND

1. Technical Field

The present disclosure relates to an ultrasound observation device observing tissue of an observed target using ultrasound, a method of operating the ultrasound observation device, and a computer-readable recording medium.

2. Related Art

In the related art, such a technique for ultrasound observation devices observing tissue as an observed target using ultrasound is known that provides correction on a received signal so as to compensate frequency dependent attenuation occurring in live body tissue (for example, see Japanese Patent Application Laid-open No. 2010-246640). This technique forms an ultrasound image using a received signal generated in a manner sequentially performing dynamic correction processing and pulse compression processing on a reflection wave from a subject based on the depth of a receiving point.

SUMMARY

In some embodiments, an ultrasound observation device includes a controller. The controller is configured to: calculate feature data of an ultrasound signal by analyzing the ultrasound signal; divide an area of interest preliminarily set on an ultrasound image into a plurality of sections; and set an attenuation rate for each of the sections; correct the attenuation rate in a range including at least a boundary between adjacent sections in a manner smoothly changing across the adjacent sections; and perform attenuation correction on the feature data using the corrected attenuation rate to calculate correction feature data.

In some embodiments, provided is a method of operating an ultrasound observation device. The method includes: calculating, by a controller, feature data of an ultrasound signal by analyzing the ultrasound signal; dividing, by the controller, an area of interest preliminarily set on an ultrasound image into a plurality of sections and setting an attenuation rate for each of the sections; correcting, by the controller, the attenuation rate in a range including at least a boundary between adjacent sections in a manner smoothly changing across the adjacent sections; and performing, by the controller, attenuation correction on the feature data using the corrected attenuation rate to calculate correction feature data.

In some embodiments, provided is a non-transitory computer-readable recording medium with an executable program stored thereon. The program is a program operating an ultrasound observation device. The program causes the ultrasound observation device to execute: calculating, by a controller, feature data of an ultrasound signal by analyzing the ultrasound signal; dividing, by the controller, an area of interest preliminarily set on an ultrasound image into a plurality of sections and setting an attenuation rate for each of the sections; correcting, by the controller, the attenuation rate in a range including at least a boundary between adjacent sections in a manner smoothly changing across the adjacent sections; and performing, by the controller, attenuation correction on the feature data using the corrected attenuation rate to calculate correction feature data.

The above and other features, advantages and technical and industrial significance of this disclosure will be better understood by reading the following detailed description of presently preferred embodiments of the disclosure, when considered in connection with the accompanying drawings.

DETAILED DESCRIPTION

Embodiments of the disclosure (hereinafter referred to as "embodiments") will now be described with reference to the accompanying drawings.

First Embodiment

Figure 1:
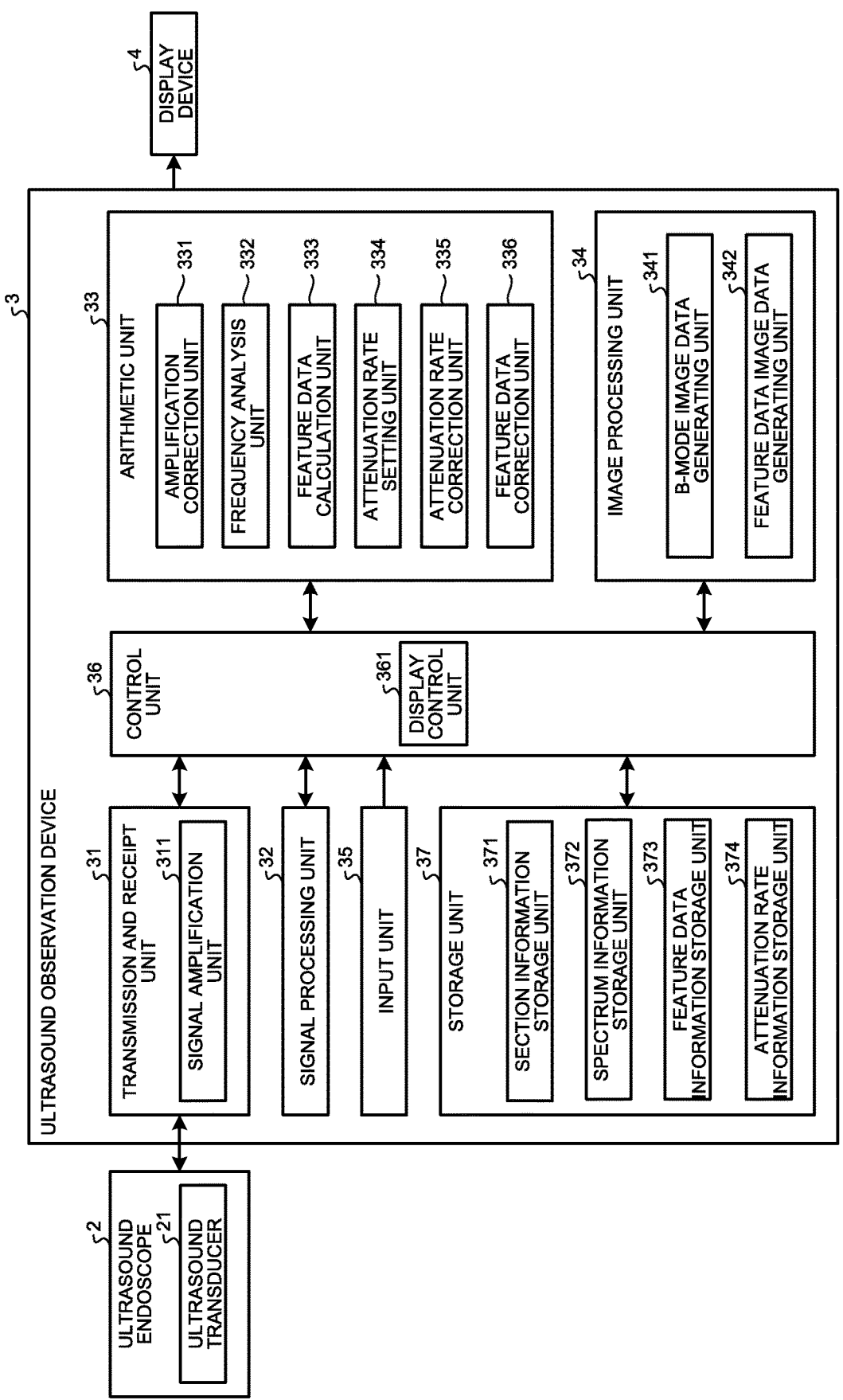
FIG. 1 is a block diagram that illustrates a functional configuration of an ultrasound diagnosis system having an ultrasound observation device according to a first embodiment of the disclosure.

FIG. 1 is a block diagram that illustrates a functional configuration of an ultrasound diagnosis system having an ultrasound observation device according to a first embodiment of the disclosure. An ultrasound diagnosis system 1 illustrated in FIG. 1 includes an ultrasound endoscope 2 transmitting ultrasound to a subject as an observed target and receiving ultrasound reflected on the subject, an ultrasound observation device 3 generating an ultrasound image based on an ultrasound signal acquired by the ultrasound endoscope 2, and a display device 4 displaying the ultrasound image generated by the ultrasound observation device 3.

The ultrasound endoscope 2 has, at its distal end, an ultrasound transducer 21 that converts an electrical pulse signal received from the ultrasound observation device 3 to an ultrasound pulse (acoustic pulse) and radiates the pulse on the subject and further converts an ultrasound echo reflected on the subject to an electrical echo signal representing the ultrasound echo in voltage variations and outputs the echo signal. Any one of a convex-type transducer, a linear-type transducer, and a radial-type transducer can be used for the ultrasound transducer 21. The ultrasound endoscope 2 may have the ultrasound transducer 21 mechanically scan or may have the ultrasound transducer 21 having a plurality of elements arranged in arrays electronically scan by electronically switching between the elements relating to transmission and receipt and delaying transmission and receipt by the elements.

The ultrasound endoscope 2 usually has an imaging optical system and imaging elements. The ultrasound endoscope 2 is inserted into the digestive tract (the esophagus, the stomach, the duodenum, and the large intestine) or the respiratory organ (the trachea and the bronchi) of a subject and is capable of capturing images of the digestive tract, the respiratory organ, and the peripheral organs (the pancreas, the gallbladder, the bile ducts, the biliary tract, the lymph nodes, the mediastinum organs, blood vessels, and others). The ultrasound endoscope 2 further has a light guide guiding illumination light radiated on the subject in imaging. The light guide has its distal end reach the distal end of an insertion unit inserted to the subject of the ultrasound endoscope 2 and has its proximal end connected to a light source device to generate illumination light.

The ultrasound observation device 3 includes a transmission and receipt unit 31, a signal processing unit 32, an arithmetic unit 33, an image processing unit 34, an input unit 35, a control unit 36, and a storage unit 37.

The transmission and receipt unit 31 is electrically connected to the ultrasound endoscope 2 and transmits a transmission signal (a pulse signal) as a high-voltage pulse to the ultrasound transducer 21 in a desired waveform at a desired transmission timing. The transmission and receipt unit 31 further receives an echo signal as an electrical received signal from the ultrasound transducer 21, generates data (hereinafter referred to as RF data) of a digital radiofrequency (RF) signal, and outputs the data. The transmission and receipt unit 31 further has a signal amplification unit 311 amplifying an echo signal. The signal amplification unit 311 performs sensitivity time control (STC) correction that amplifies an echo signal having a larger receiving depth at a higher amplification rate.

Figure 2:
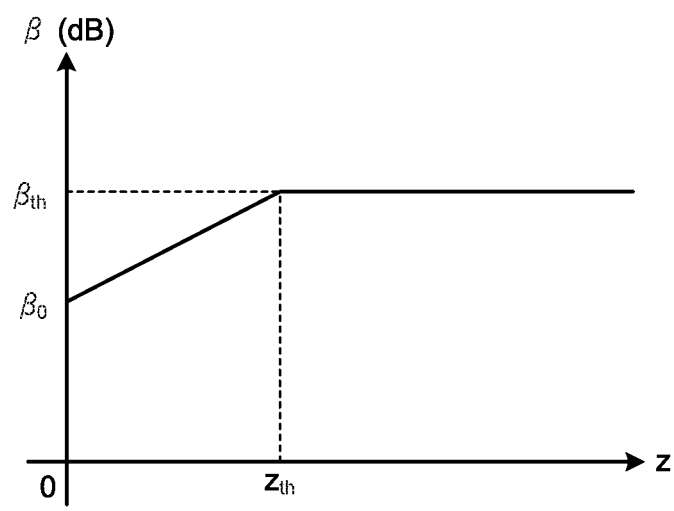
FIG. 2 is a drawing that illustrates relation between a receiving depth and an amplification rate in amplification processing performed by a signal amplification unit of the ultrasound observation device according to the first embodiment of the disclosure.

FIG. 2 is a drawing that illustrates relation between a receiving depth and an amplification rate in amplification processing performed by the signal amplification unit 311. A receiving depth z illustrated in FIG. 2 is an amount calculated based on a time elapsed since a start of receiving ultrasound. As illustrated in FIG. 2, an amplification rate $\beta$ (dB) linearly increases from $\beta_0$ to $\beta_{th}$ ($>\beta_0$) with an increase in the receiving depth z when the receiving depth z is smaller than a threshold $z_{th}$. The amplification rate $\beta$ (dB) takes a constant value $\beta_{th}$ when the receiving depth z is equal to or greater than the threshold $z_{th}$. The threshold $z_{th}$ is a value at which an ultrasound signal received from the observed target mostly attenuates and noise becomes dominant. In general, the amplification rate $\beta$ may regularly increase with an increase in the receiving depth z when the receiving depth z is smaller than the threshold $z_{th}$. The relation illustrated in FIG. 2 is preliminarily stored in the storage unit 37.

The transmission and receipt unit 31 performs processing such as filtering on the echo signal amplified by the signal amplification unit 311, generates RF data in the time domain by A/D conversion, and outputs the data to the signal processing unit 32 and the arithmetic unit 33. If the ultrasound endoscope 2 is configured such that the ultrasound transducer 21 having a plurality of elements arranged in arrays electronically scans, the transmission and receipt unit 31 has a multi-channel circuit for beam formation for the elements.

The bandwidth of a pulse signal transmitted from the transmission and receipt unit 31 may be sufficiently wide to substantially cover the linear response bandwidth for electro-acoustic conversion from a pulse signal to an ultrasound pulse in the ultrasound transducer 21. Furthermore, the various processing bandwidths for an echo signal of the signal amplification unit 311 may be sufficiently wide to substantially cover the linear response bandwidth for acoustic-electro conversion from an ultrasound echo to an echo signal by the ultrasound transducer 21. These manners allow more accurate approximation in performing the later-described approximation processing on a frequency spectrum.

The transmission and receipt unit 31 further has functions of transmitting various control signals output from the control unit 36 to the ultrasound endoscope 2 and of receiving various kinds of information including IDs for identification from the ultrasound endoscope 2 and transmitting the information to the control unit 36.

The signal processing unit 32 generates digital B-mode receiving data based on RF data received from the transmission and receipt unit 31. More specifically, the signal processing unit 32 generates digital B-mode receiving data by providing known processing such as bandpass filtering, envelope detection, and logarithmic transformation on the RF data. In the logarithmic transformation, the common logarithm to the quantity of RF data divided by standard voltage is expressed in decibels. The signal processing unit 32 outputs the generated B-mode receiving data to the image processing unit 34. The signal processing unit 32 is implemented by using a general-purpose processor such as a central processing unit (CPU), a dedicated integrated circuit implementing specific functions such as an application specific integrated circuit (ASIC) and a field programmable gate array (FPGA), or the like.

The arithmetic unit 33 gives certain arithmetic calculation on the RF data received from the transmission and receipt unit 31. The arithmetic unit 33 includes an amplification correction unit 331, a frequency analysis unit 332, a feature data calculation unit 333, an attenuation rate setting unit 334, an attenuation rate correction unit 335, and a feature data correction unit 336. The arithmetic unit 33 is implemented by using a general-purpose processor such as a CPU, a dedicated integrated circuit such as an ASIC and a FPGA, or the like.

Figure 3:
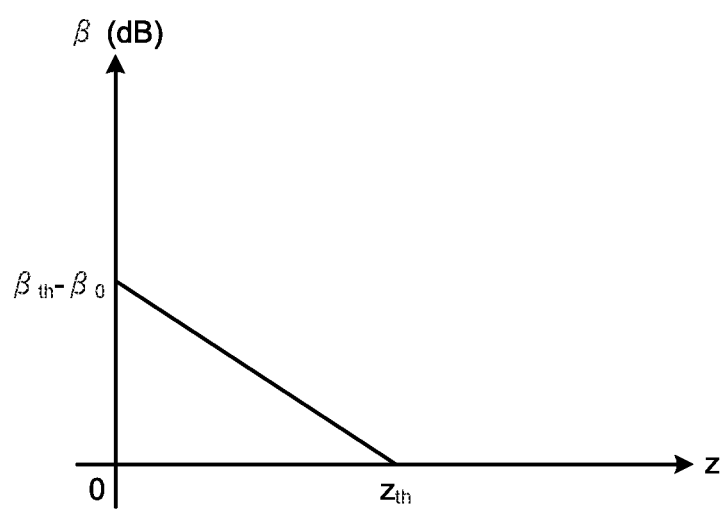
FIG. 3 is a drawing that illustrates relation between a receiving depth and an amplification rate in amplification correction processing performed by an amplification correction unit of the ultrasound observation device according to the first embodiment of the disclosure.

The amplification correction unit 331 provides amplification correction on the RF data output from the transmission and receipt unit 31 in a manner having the amplification rate constant regardless of the receiving depth. FIG. 3 is a drawing that illustrates relation between the receiving depth and the amplification rate in amplification correction processing performed by the amplification correction unit 331. As illustrated in FIG. 3, the amplification rate β (dB) in the amplification correction processing performed by the amplification correction unit 331 takes the maximum value $\beta_{th}-\beta_0$ when the receiving depth z is zero, linearly decreases until the receiving depth z increases to the threshold $z_{th}$ from zero, and becomes zero with the receiving depth z equal to or greater than the threshold $z_{th}$. The relation illustrated in FIG. 3 is preliminarily stored in the storage unit 37. The amplification correction unit 331 performs amplification correction on the digital RF signal based on the relation illustrated in FIG. 3. With this correction, the amplification correction unit 331 is able to offset the effect of the sensitivity time control (STC) correction by the signal amplification unit 311 and to output a signal having a constant amplification rate $\beta_{th}$. The relation between the receiving depth z and the amplification rate β in the amplification correction unit 331 varies depending on the relation between the receiving depth and the amplification rate in the signal amplification unit 311.

A reason why the amplification correction is necessary will now be described. The STC correction is correction processing to remove the effect of attenuation from the amplitude of an analogue signal waveform by amplifying the amplitude of the analogue signal waveform uniformly over the entire bandwidth and at an amplification rate allowing a regular increase for the depth. The STC correction makes a brightness value constant regardless of the depth in the case of generating a B-mode image displayed with the amplitude of an echo signal converted to brightness and in the case of scanning uniform tissue. In other words, the STC correction can remove effects of attenuation from a brightness value of a B-mode image.

When using results of calculation and analysis of an ultrasound frequency spectrum as described in the first embodiment, however, the STC correction is not always capable of accurately removing effects of attenuation caused with ultrasound propagating. This is because the amount of attenuation usually varies depending on a frequency (see the later-described formula (1)), whereas the amplification rate in the STC correction varies depending on the distance only and has no frequency dependence. A possible solution to this problem is that a received signal with the STC correction performed thereon is output in generating a B-mode image, whereas a received signal with no STC correction performed thereon is output through another transmission process different from transmission for generating the B-mode image in generating an image based on a frequency spectrum. In this case, however, the frame rate of image data generated based on the received signal is problematically decreased. In the first embodiment, the amplification correction unit 331 thus corrects the amplification rate so as to remove effects of the STC correction from a signal having undergone the STC correction to create a B-mode image while keeping the frame rate of generated image data.

The frequency analysis unit 332 calculates a plurality of frequency spectra corresponding to the receiving depths and the receiving directions of an ultrasound signal by analyzing the frequency of the ultrasound signal. More specifically, the frequency analysis unit 332 calculates frequency spectra at a plurality of points (data positions) on RF data by generating sample data by sampling RF data (line data) of a sound ray having undergone the amplification correction by the amplification correction unit 331 at predetermined time intervals and performing the Fast Fourier Transform (FFT) processing on sample data groups.

Figure 4:
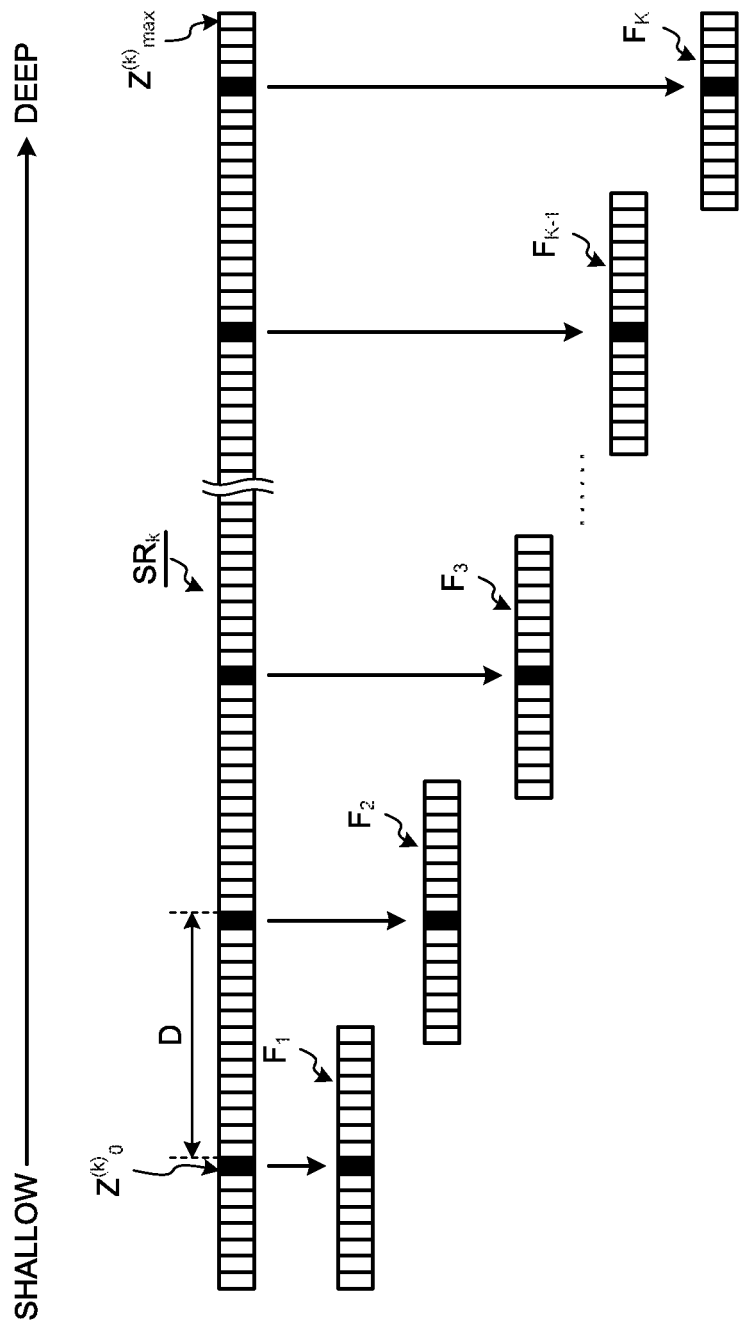
FIG. 4 is a drawing that schematically illustrates a data array on a sound ray of an ultrasound signal.

FIG. 4 is a drawing that schematically illustrates a data array on a sound ray of an ultrasound signal. On the sound ray $SR_k$ illustrated in FIG. 4, a rectangular cell in white or in black represents data at a sampling point. Furthermore, on the sound ray $SR_k$, data situated closer to the right side is sample data obtained from a deeper point in measurement from the ultrasound transducer 21 along the $SR_k$ (see the arrows in FIG. 4). The sound ray $SR_k$ is discretized at time intervals corresponding to a sampling frequency (for example, 50 MHz) in A/D conversion performed by the transmission and receipt unit 31. In FIG. 4, the eighth data position on the sound ray $SR_k$ of number k is set as an initial value $Z^{(k)}_0$ in a direction of the receiving depth z. Instead of this, any position of an initial value can be set. Results of calculation by the frequency analysis unit 332 are obtained in complex numbers and stored in the storage unit 37.

The data group $F_j$ (j=1, 2, ..., K) illustrated in FIG. 4 is a sample data group on which the FFT processing is performed. For the FFT processing, a sample data group generally needs to include data pieces expressed in powers of two. In this meaning, the sample data group $F_j$ (j=1, 2, ..., K−1) is a normal data group that includes 16 (=$2^4$) data pieces, whereas the sample data group $F_K$ is an abnormal data group that includes 12 data pieces. When the FFT processing is performed on such an abnormal data group, processing for generating a normal sample data group is performed by adding zero data for the shortage. This process will be described later in detail along with description of the processing performed by the frequency analysis unit 332 (see FIG. 11).

Figure 5:
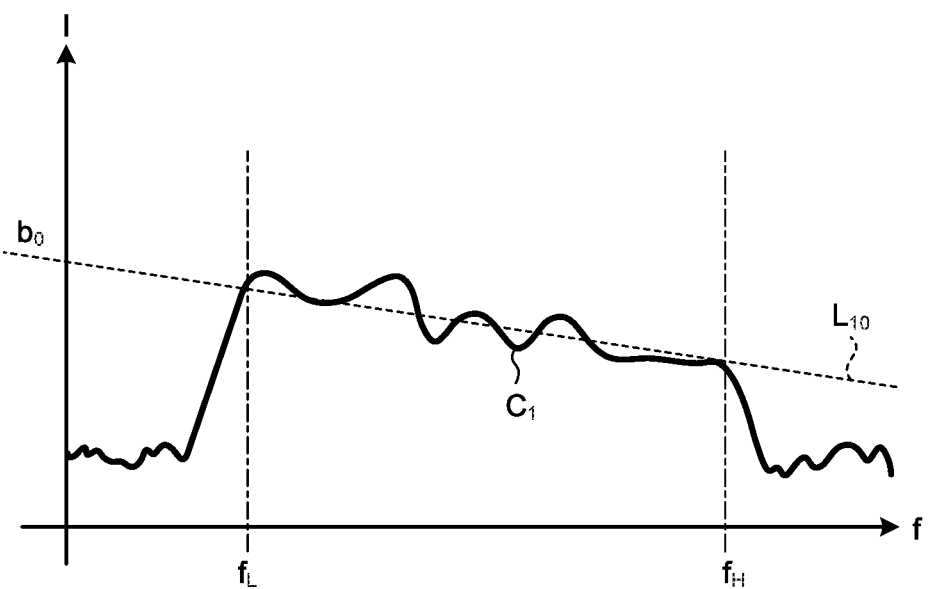
FIG. 5 is a drawing that illustrates an exemplary frequency spectrum calculated by a frequency analysis unit of the ultrasound observation device according to the first embodiment of the disclosure.

FIG. 5 is a drawing that illustrates an exemplary frequency spectrum calculated by the frequency analysis unit 332. The term "frequency spectrum" in this case indicates "a frequency distribution of intensity at a receiving depth z", which is obtained by performing the FFT processing on a sample data group. The term "intensity" indicates, for example, any one of a parameter such as voltage of an echo signal, power of an echo signal, the sound pressure of an ultrasound echo, and acoustic energy of an ultrasound echo, the amplitude, a time integral value, and a combination thereof of the parameter.

In FIG. 5, the abscissa gives a frequency f. Furthermore, in FIG. 5, the ordinate gives a common logarithm (in decibels) for the quantity of intensity $I_0$ divided by standard intensity $I_c$ (a constant), which is: $I = 10 \log_{10}(I_0/I_c)$. In FIG. 5, the receiving depth z is constant. A straight line $L_{10}$ in FIG. 5 will be described later. Curved lines of frequency spectra illustrated in FIG. 5 and FIG. 7, which is described later, and straight lines relative to the curved lines consist of sets of discrete points.

On a frequency spectrum $C_1$ illustrated in FIG. 5, a lower frequency limit $f_L$ and an upper frequency limit $f_H$ of a bandwidth used in further calculation are parameters determined based on the bandwidth of the ultrasound transducer 21, the bandwidth of a pulse signal transmitted from the transmission and receipt unit 31, and others. For example, $f_L = 3$ MHz and $f_H = 10$ MHz are given. In FIG. 5, the bandwidth defined by the lower frequency limit $f_L$ and the upper frequency limit $f_H$ will be referred to as a "bandwidth U".

If an observed target is live tissue, a frequency spectrum generally exhibits different trends depending on the characteristics of the live tissue scanned by ultrasound. This is because the frequency spectrum is correlated with the size, the number density, and the acoustic impedance of a scattering body that scatters ultrasound. Examples of the "characteristics of live tissue" in this case include a malignant tumor (cancer), a benign tumor, an endocrine tumor, a mucinous tumor, normal tissue, a cyst, and a vascular vessel.

The feature data calculation unit 333 calculates feature data of each frequency spectrum. More specifically, the feature data calculation unit 333 provides regression analysis on a frequency spectrum in a predetermined bandwidth and approximates the spectrum using a linear formula. With this method, the feature data calculation unit 333 calculates feature data characterizing the linear formula used for approximation. For example, on the frequency spectrum $C_1$ illustrated in FIG. 5, the feature data calculation unit 333 acquires an approximate straight line $L_{10}$ by providing regression analysis on the bandwidth U. In expression of the approximate straight line $L_{10}$ using a linear formula of the frequency f: $I = a_0 f + b_0$, the feature data calculation unit 333 calculates a slope $a_0$, an intercept $b_0$, and a mid-band fit: $c_0 = a_0 f_M + b_0$, which is a value of intensity I for the center frequency of the bandwidth U: $f_M = (f_L + f_H)/2$, as feature data corresponding to the straight line $L_{10}$. The feature data calculation unit 333 may approximate a frequency spectrum using a polynomial of degree two or greater.

Among three pre-correction feature data pieces, the slope $a_0$ is correlated with the size of a scattering body of ultrasound and is generally considered to have a smaller value for a larger scattering body. The intercept $b_0$ is correlated with the size of a scattering body, a variance in acoustic impedance, the number density (the concentration) of a scattering body, and others. More specifically, the intercept $b_0$ is considered to have a larger value for a larger scattering body, has a larger value for a larger variance in acoustic impedance, and has a larger value for a larger number density of a scattering body. The mid-band fit $c_0$ is an indirect parameter derived from the slope $a_0$ and the intercept $b_0$ and giving intensity of the spectrum in the center of the bandwidth U. The mid-band fit $c_0$ is therefore considered to have correlation with brightness of a B-mode image to some extent other than with the size of a scattering body, a variance in acoustic impedance, and the number density of a scattering body.

The attenuation rate setting unit 334 sets an attenuation rate that gives attenuation characteristics to the ultrasound propagating through an observed target in an area of interest set on an ultrasound image. In the first embodiment, the area of interest may be preliminarily set. In another manner, the input unit 35 may receive an input of a setting signal relating to the position, the size, and the shape of an area of interest, and the arithmetic unit 33 may set the area of interest based on the setting signal.

Processing performed by the attenuation rate setting unit 334 will now be described in detail. The attenuation rate setting unit 334 divides an area of interest into a plurality of sections. The attenuation rate setting unit 334 thereafter uses a plurality of attenuation rate candidate values per unit length and per unit frequency that give respective different attenuation characteristics to the ultrasound propagating through an observed target and performs attenuation correction for removing effects of ultrasound on the feature data of each frequency spectrum, in each section. In this manner, the attenuation rate setting unit 334 calculates preliminary correction feature data of a frequency spectrum for each attenuation rate candidate value. The attenuation rate setting unit 334 thereafter sets an optimal attenuation rate to the observed target among the attenuation rate candidate values based on the results of calculation of preliminary correction feature data.

Figure 6:
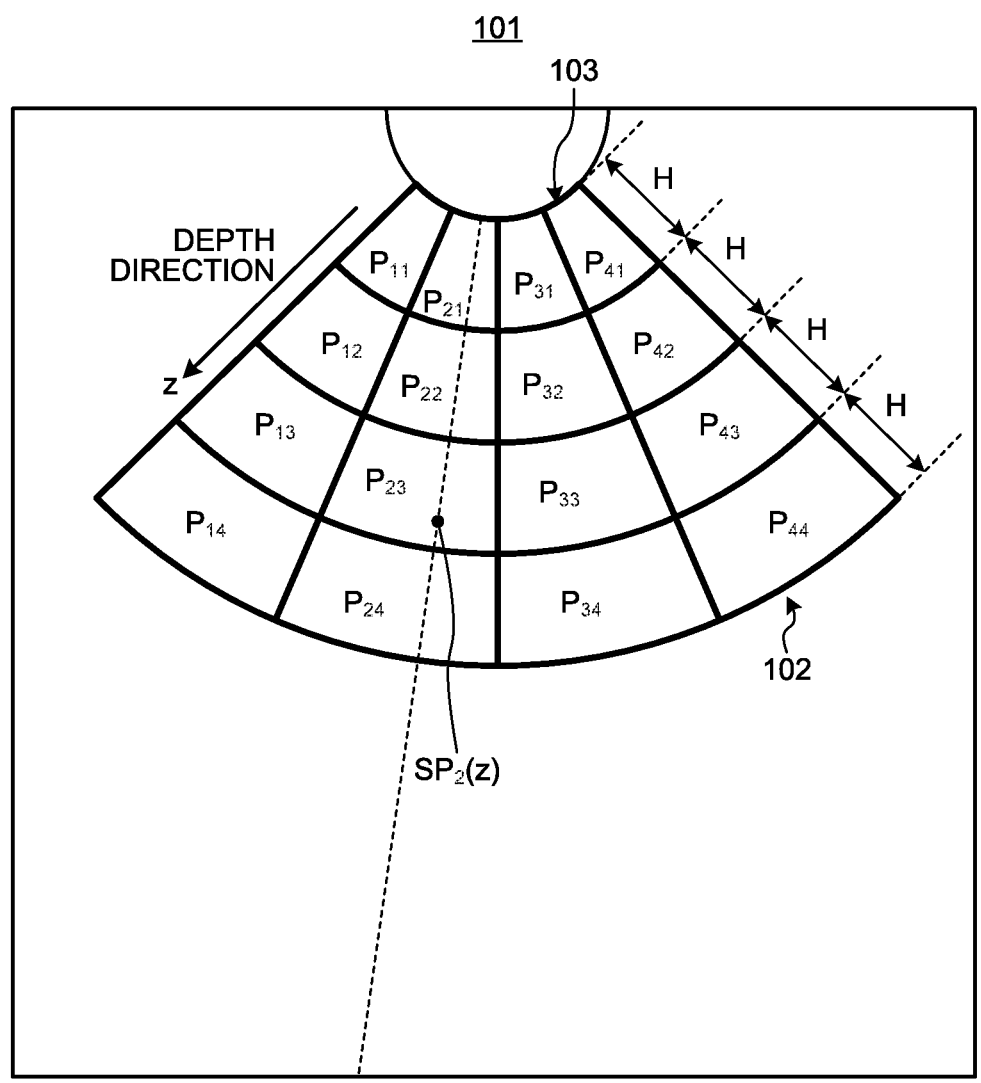
FIG. 6 is a drawing that schematically illustrates exemplary arrangement of sections divided in an area of interest in a display area of an ultrasound image.

FIG. 6 is a drawing that schematically illustrates exemplary arrangement of sections divided in an area of interest in a display area of an ultrasound image. In FIG. 6, one sound ray is simply illustrated by a broken line, although a plurality of sound rays are usually arranged at certain intervals along the scan direction (the circumferential direction of an area of interest 102 illustrated in FIG. 6).

In FIG. 6, the substantially fan-shaped area of interest 102 in an image display area 101 is divided into 16 sections $P_{ij}$ (i=1 to 4, j=1 to 4). All the sections $P_{ij}$ have the same height H in a direction of receiving depth (the depth direction) radially extending from a surface position 103 of the ultrasound transducer 21 in the image display area 101. Information about the manner of dividing the area of interest into sections is stored in a section information storage unit 371 of the storage unit 37. This information further includes, for example, relation between the area of interest and a section in size and/or in shape. When the area of interest is set, the attenuation rate setting unit 334 sets sections based on the area of interest by referring to the section information storage unit 371. In FIG. 6, the ultrasound transducer 21 is illustrated as a convex-type transducer; however, any type of ultrasound transducer 21 is applicable to set the sections. The number of sections illustrated in FIG. 6 is merely an example, and the number is changed based on conditions such as the size of the area of interest. The whole area of the ultrasound image is usable as one area of interest.

An attenuation amount A (f, z) of ultrasound is generally attenuation caused while ultrasound moves (proceeds and returns) between the receiving depth zero and the receiving depth z and is defined as an intensity variance (a variance in decibels) before and after the move. The attenuation amount A (f, z) is experimentally known to be proportional to a frequency in uniform tissue and is expressed by the following formula (1).

$$A(f,z)=2\alpha z f \quad (1)$$

The proportional constant α denotes an amount referred to as an attenuation rate and gives the attenuation amount of ultrasound per unit length and per unit frequency. In the formula, z denotes receiving depth of ultrasound, and f denotes frequency. If the observed target is a live body, the value of the attenuation rate α is determined according to a site of the live body. The unit of measurement of the attenuation rate α is, for example, dB/cm/MHz.

The attenuation rate setting unit 334 sets an optimal attenuation rate among a plurality of attenuation rate candidate values. Specifically, the attenuation rate setting unit 334 provides attenuation correction on the feature data (the slope $a_0$, the intercept $b_0$, and the mid-band fit $c_0$) calculated by the feature data calculation unit 333 by using the attenuation rate candidate value α for the following formulae (2) to (4) and calculates preliminary correction feature data a, b, and c.

$$a=a_0+2\alpha z \quad (2)$$

$$b=b_0 \quad (3)$$

$$c=c_0+A(f_M,z)=c_0+2\alpha z f_M(=af_M+b) \quad (4)$$

According to the formulae (2) and (4), the attenuation rate setting unit 334 provides correction with a larger correction amount for a larger receiving depth z of ultrasound. According to the formula (3), correction relative to the intercept $b_0$ uses identity transformation because the intercept is a frequency element corresponding to a frequency of zero (Hz) under no effects of attenuation.

Figure 7:
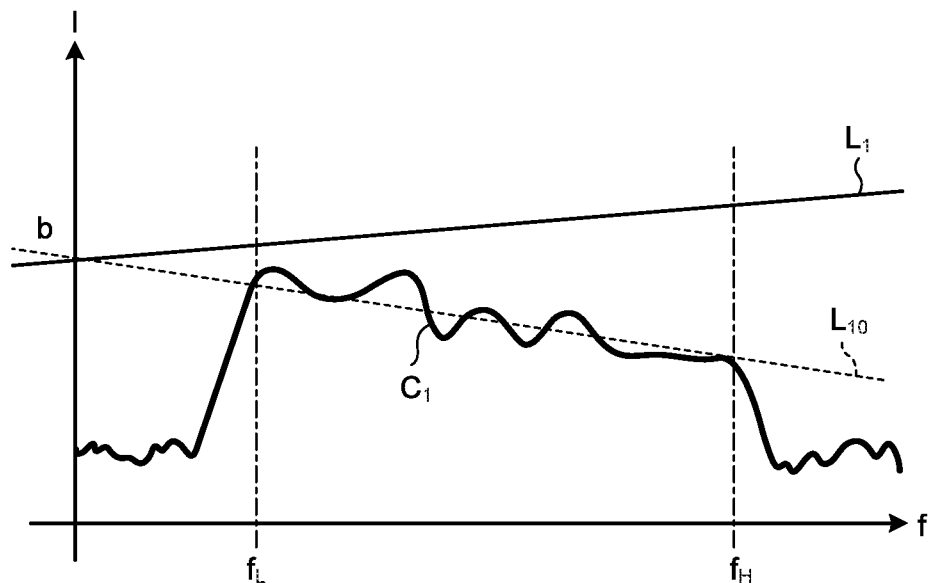
FIG. 7 is a drawing that illustrates a straight line having preliminary correction feature data corrected by an attenuation rate setting unit of the ultrasound observation device according to the first embodiment of the disclosure as parameters.

FIG. 7 is a drawing that illustrates a straight line having preliminary correction feature data a, b, and c corrected by the attenuation rate setting unit 334 as parameters. A straight line $L_1$ is expressed by the following formula (5).

$$I=af+b=(a_0+2\alpha z)f+b_0 \quad (5)$$

According to the formula (5), the straight line $L_1$ has a larger slope ($a>a_0$) than that of the straight line $L_{10}$ before attenuation correction and has the same intercept ($b=b_0$) as that of the straight line $L_{10}$.

The attenuation rate setting unit 334 sets an attenuation rate candidate value allowing minimal statistical dispersion of preliminary correction feature data calculated using an attenuation rate candidate value as an optimal attenuation rate, for each section. In the first embodiment, variance is used to quantify statistical dispersion. In this case, the attenuation rate setting unit 334 sets an attenuation rate candidate value allowing minimal variance as an optimal attenuation rate. Among the above-described three preliminary correction feature data pieces a, b, and c, two data pieces are independent. In addition, the preliminary correction feature data b is not dependent on the attenuation rate. In setting an optimal attenuation rate for the preliminary correction feature data a and c, the attenuation rate setting unit 334 only needs to calculate variance of either one of the preliminary correction feature data a and c.

When the attenuation rate setting unit 334 sets an optimal attenuation rate using preliminary correction feature data a, the attenuation rate setting unit 334 preferably uses variance of the preliminary correction feature data a. Likewise, the attenuation rate setting unit 334 preferably uses variance of preliminary correction feature data c for setting an optimal attenuation value using the preliminary correction feature data c. As a reason of this, the formula (1) giving the amount of attenuation A (f, z) is merely ideal, and the following formula (6) is actually more appropriate.

$$A(f,z)=2\alpha z f+2\alpha_1 z \quad (6)$$

The second term $\alpha_1$ in the right side of the formula (6) is a coefficient expressing the magnitude of a change in signal intensity in proportional to the receiving depth z of ultrasound. The coefficient expresses a change in signal intensity that results from non-uniform tissue as an observed target, a change in the number of channels in beam formation, and other factors. Because of the second term in the right side of the formula (6), use of variance of the preliminary correction feature data c in setting an optimal attenuation rate using the preliminary correction feature data c allows more accurate correction of attenuation (see the formula (4)). When setting an optimal attenuation rate using the preliminary correction feature data a as a coefficient proportional to the frequency f, use of variance of the preliminary correction feature data a allows more accurate correction of attenuation by removing the effects of the second term in the right side of the formula (6).

A reason why an optimal attenuation rate can be set using statistical dispersion will now be described. When an attenuation rate optimal to an observed target is applied, statistical dispersion is considered to be reduced because the feature data converges to a value unique to the target regardless of the distance between the target and the ultrasound transducer 21. On the other hand, use of an attenuation rate candidate value not adapted to the target as an optimal attenuation rate renders attenuation to be excessively or insufficiently corrected. This results in a variance in feature data depending on the distance from the ultrasound transducer 21, and statistical dispersion of the feature data is therefore considered to be increased. Consequently, an attenuation rate candidate value allowing minimal statistical dispersion is considered to be an optimal attenuation rate for the observed target.

Figure 8:
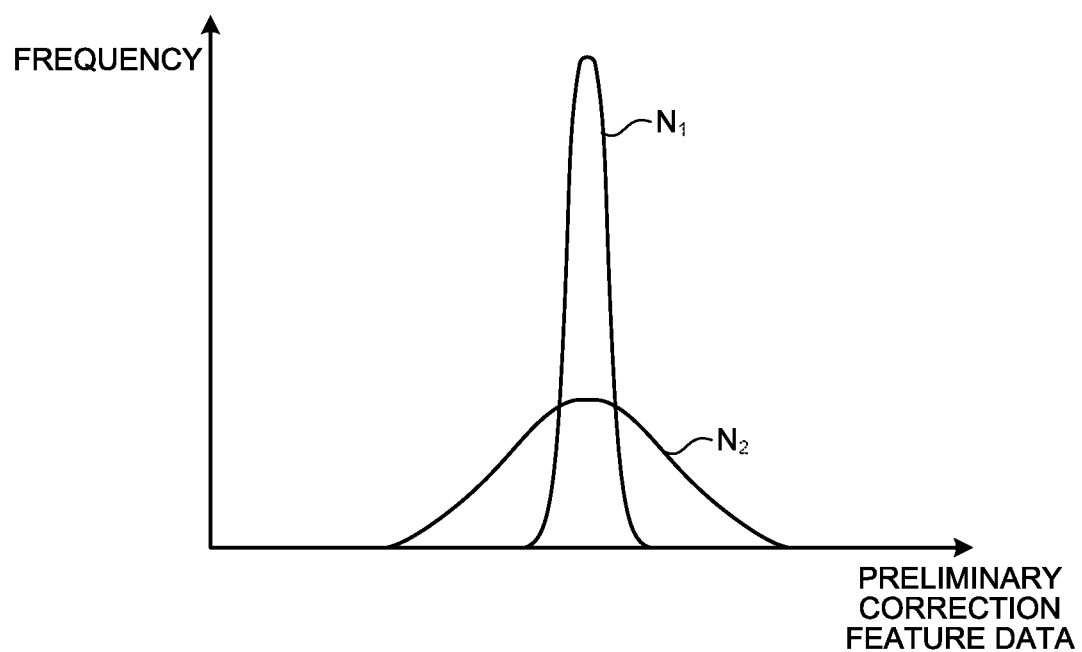
FIG. 8 is a drawing that schematically illustrates exemplary distributions of preliminary correction feature data having undergone attenuation correction based on two different attenuation rate candidate values for the same observed target.

FIG. 8 is a drawing that schematically illustrates exemplary distributions of preliminary correction feature data having undergone attenuation correction based on two different attenuation rate candidate values for the same observed target. In FIG. 8, the abscissa gives the preliminary correction feature data, and the ordinate gives the frequency. The two distribution curved lines $N_1$ and $N_2$ illustrated in FIG. 8 have the same sum of frequency. In FIG. 8, the distribution curved line $N_1$ has small statistical dispersion of feature data (small variance) compared to the distribution curved line $N_2$ and forms a steep mountain. When the attenuation rate setting unit 334 sets an optimal attenuation rate from two attenuation rate candidate values corresponding to respective two distribution curved lines $N_1$ and $N_2$, the attenuation rate setting unit 334 sets an attenuation rate candidate value corresponding to the distribution curved line $N_1$ as an optimal attenuation rate.

The attenuation rate correction unit 335 corrects the optimal attenuation rate set by the attenuation rate setting unit 334 such that the attenuation rate smoothly changes in the vicinity of a boundary between sections. More specifically, the attenuation rate correction unit 335 performs processing to smooth a change in the attenuation rate in the vicinity of a boundary between sections by providing linear interpolation using straight lines on the optimal attenuation rate.

Figure 9:
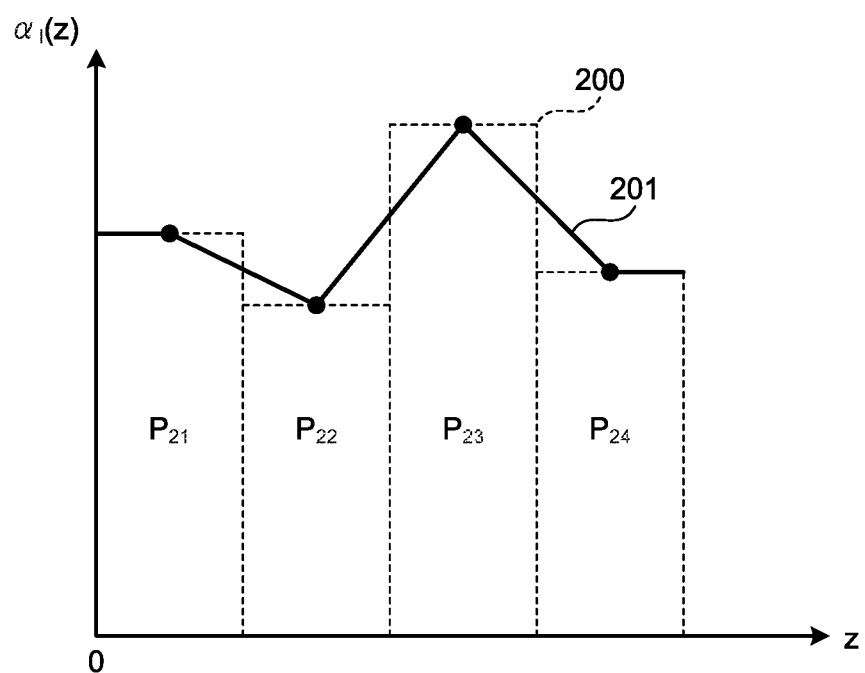
FIG. 9 is a drawing that illustrates an overview of correction processing performed by an attenuation rate correction unit of the ultrasound observation device according to the first embodiment of the disclosure.

FIG. 9 is a drawing that illustrates an overview of correction processing performed by the attenuation rate correction unit 335. In FIG. 9, the abscissa gives the receiving depth z of an ultrasound image, whereas the ordinate gives the optimal attenuation rate $\alpha_I(z)$ in a section $P_{Ij}(z)$. A histogram 200 indicated by broken lines represents the optimal attenuation rate $\alpha_I(z)$ for a receiving depth z in a section $P_{Ij}$ (I=a constant of 1 to 4, j=1 to 4) that has a sound ray pass. FIG. 9 illustrates an example where I=2 is given. A curved line 201 represents relation between the receiving depth z and the optimal attenuation rate $\alpha_I(z)$ after linear interpolation processing by the attenuation rate correction unit 335. The attenuation rate correction unit 335 performs linear interpolation connecting between center positions of adjacent sections with a straight line. This processing smooths a change in the optimal attenuation rate $\alpha_I(z)$ across adjacent sections.

In this example, the attenuation rate correction unit 335 corrects the optimal attenuation rate along the depth direction. In another manner, the attenuation rate correction unit 335 may correct a change in the optimal attenuation rate across adjacent sections along a scan direction of the ultrasound transducer 21. The attenuation rate correction unit 335 may correct a change in the optimal attenuation rate across adjacent sections along the depth direction and along the scan direction.

The feature data correction unit 336 calculates correction feature data in an area of interest of an ultrasound image by providing attenuation correction on feature data using the attenuation rate corrected by the attenuation rate correction unit 335. The feature data correction unit 336 calculates a cumulative attenuation rate (simply referred to as a cumulative attenuation rate) per unit frequency at a sampling point using an optimal attenuation rate for a section situated between a surface position of an ultrasound transducer and the sampling point among optimal attenuation rates for the respective sections and corrects attenuation of feature data using the cumulative attenuation rate. The cumulative attenuation rate at any sampling point is calculated using the distance from the surface of the ultrasound transducer 21 and an optimal attenuation rate for a section situated between the surface and the sampling point. A cumulative attenuation rate $\gamma_I(z)$ at a sampling point $SP_I(z)$ included in a section $P_{Ij}$ and representing a distance z from the surface position of the ultrasound transducer 21 is expressed by the following formula (7).

$$\gamma_I(z) \int_0^z \alpha_I(z')dz' \quad (7)$$

The number 2 in the right side of the formula (7) indicates a round-trip distance between the surface position of the ultrasound transducer and the sampling point z. In this manner, the feature data correction unit 336 calculates the cumulative attenuation rate $\gamma_I(z)$ by accumulating the attenuation rates from the surface of the ultrasound transducer 21. When a unit of measurement dB/cm/MHz is used as an optimal attenuation rate, a unit of measurement for the cumulative attenuation rate is dB/MHz.

The feature data correction unit 336 corrects attenuation of feature data at a sampling point $SP_I(z)$ using the cumulative attenuation rate $\gamma_I(z)$ as follows.

$$a_I(z) = a_0 + 2\gamma_I(z) \quad (8)$$

$$b_I(z) = b_0 \quad (9)$$

$$c_I(z) = c_0 + 2f_M \gamma_I(z) \quad (10)$$

The image processing unit 34 generates various kinds of image data. Specifically, the image processing unit 34 includes a B-mode image data generating unit 341 and a feature data image data generating unit 342. The image processing unit 34 is implemented by using a general-purpose processor such as a CPU, a dedicated integrated circuit such as an ASIC and a FPGA, or the like.

The B-mode image data generating unit 341 generates B-mode image data as ultrasound image data displayed with the amplitude of an echo signal converted to brightness. Specifically, the B-mode image data generating unit 341 generates B-mode image data by, for example, providing signal processing using known techniques such as gain processing and contrast processing on B-mode receiving data received from the signal processing unit 32 and decimating data based on a data step width determined based on a display range of an image of the display device 4. The B-mode image is a grayscale image where values of R (red), G (green), and B (blue), as variables on the RGB color model adapted for a color space, coincide with one another.

The B-mode image data generating unit 341 generates B-mode image data by providing coordinate transformation on the B-mode receiving data in a manner rearranging the coordinates to obtain more spatially correct expression of the scan range and providing interpolation processing between B-mode receiving data pieces so as to fill a gap therebetween. The B-mode image data generating unit 341 outputs the generated B-mode image data to the feature data image data generating unit 342.

The feature data image data generating unit 342 generates feature data image data that displays information relating to correction feature data calculated by the feature data correction unit 336. Specifically, the feature data image data generating unit 342 generates feature data image data by overlapping visual information relating to the correction feature data calculated by the feature data correction unit 336 on each pixel of an image of the B-mode image data. For example, the feature data image data generating unit 342 allocates visual information corresponding to feature data of a frequency spectrum calculated from a sample data group $F_j$ (j=1, 2, . . . , K) illustrated in FIG. 4 to a pixel area corresponding to the data amount of the sample data group F. The feature data image data generating unit 342 generates feature data image data by relating, for example, hue included in the visual information to any one of the above-described slope, intercept, and mid-band fit. In another manner, the feature data image data generating unit 342 may generate feature data image data by relating hue to either one of two feature data pieces selected among the slope, the intercept, and the mid-band fit and relating contrast to the other one. Examples of the visual information relating to feature data include saturation, a brightness value, a variable such as R (red), G (green), and B (blue) of a color space having a certain color model, other than hue and contrast (luminosity).

The input unit 35 receives input of various kinds of information including an operation instruction signal of the ultrasound observation device 3. For example, the input unit 35 receives an input for setting an area of interest, which is a partial area sectioned based on a certain depth width and a sound ray width on an ultrasound image. The input unit 35 is configured with a user interface such as a keyboard, a mouse, a trackball, and a touchscreen.

The control unit 36 integrally controls operation of the ultrasound diagnosis system 1. The control unit 36 includes a display control unit 361 that controls display of the display device 4. The display control unit 361 controls the display device 4 to display images corresponding to B-mode image data generated by the B-mode image data generating unit 341 and feature data image data generated by the feature data image data generating unit 342. The display control unit 361 is also able to control the display device 4 to display the B-mode image and the feature data image next to each other.

The control unit 36 is implemented by a general processor such as a CPU having arithmetic and control functions, a dedicated integrated circuit such as an ASIC and an FPGA, and the like. If the control unit 36 is implemented by a general processor or an FPGA, the control unit 36 integrally controls the ultrasound observation device 3 by reading out various computer programs and various data stored in the storage unit 37 from the storage unit 37 and performing various arithmetic processing relating to a method for operating the ultrasound observation device 3. If the control unit 36 is configured with an ASIC, the control unit 36 may execute various processing by itself or execute various processing by using various data stored in the storage unit 37. The control unit 36 may share a general processor, a dedicated integrated circuit, or the like with the signal processing unit 32, the arithmetic unit 33, and the image processing unit 34.

The storage unit 37 stores various information including information necessary for operation of the ultrasound observation device 3. The storage unit 37 includes the section information storage unit 371 storing information relating to sections, a spectrum information storage unit 372 storing information about a frequency spectrum calculated by the frequency analysis unit 332 along with the receiving depth and the receiving direction, a feature data information storage unit 373 storing information relating to feature data calculated by the feature data calculation unit 333 and correction feature data corrected by the feature data correction unit 336, and an attenuation rate information storage unit 374 storing information relating to an optimal attenuation rate set by the attenuation rate setting unit 334 for each section and a cumulative attenuation rate calculated by the feature data correction unit 336 for each sampling point.

Other than the above-listed information, the storage unit 37 stores, for example, information (relation between the amplification rate and the receiving depth illustrated in FIG. 2) necessary for amplification processing, information (relation between the amplification rate and the receiving depth illustrated in FIG. 3) necessary for amplification correction processing, information (see the formula (1)) necessary for attenuation correction processing, and information about a window function (such as Hamming window, Hanning window, and Blackman window) necessary for frequency analysis processing.

The storage unit 37 stores therein various computer programs including an operation program for implementing a method for operating the ultrasound observation device 3. The operation program can be recorded in a computer-readable recording medium such as a hard disk, a flash memory, a CD-ROM, a DVD-ROM, and a flexible disk for wider distribution. The above-described various computer programs are available by downloading the programs through a communication network. The communication network is implemented by, for example, an existing public network, a local area network (LAN), and a wide area network (WAN) regardless of whether wired or wireless.

The storage unit 37 having the above-described configuration is implemented by using, for example, a read only memory (ROM) to which various computer programs and others are preliminarily installed and a random access memory (RAM) storing arithmetic parameters and data of processing and others.

Figure 10:
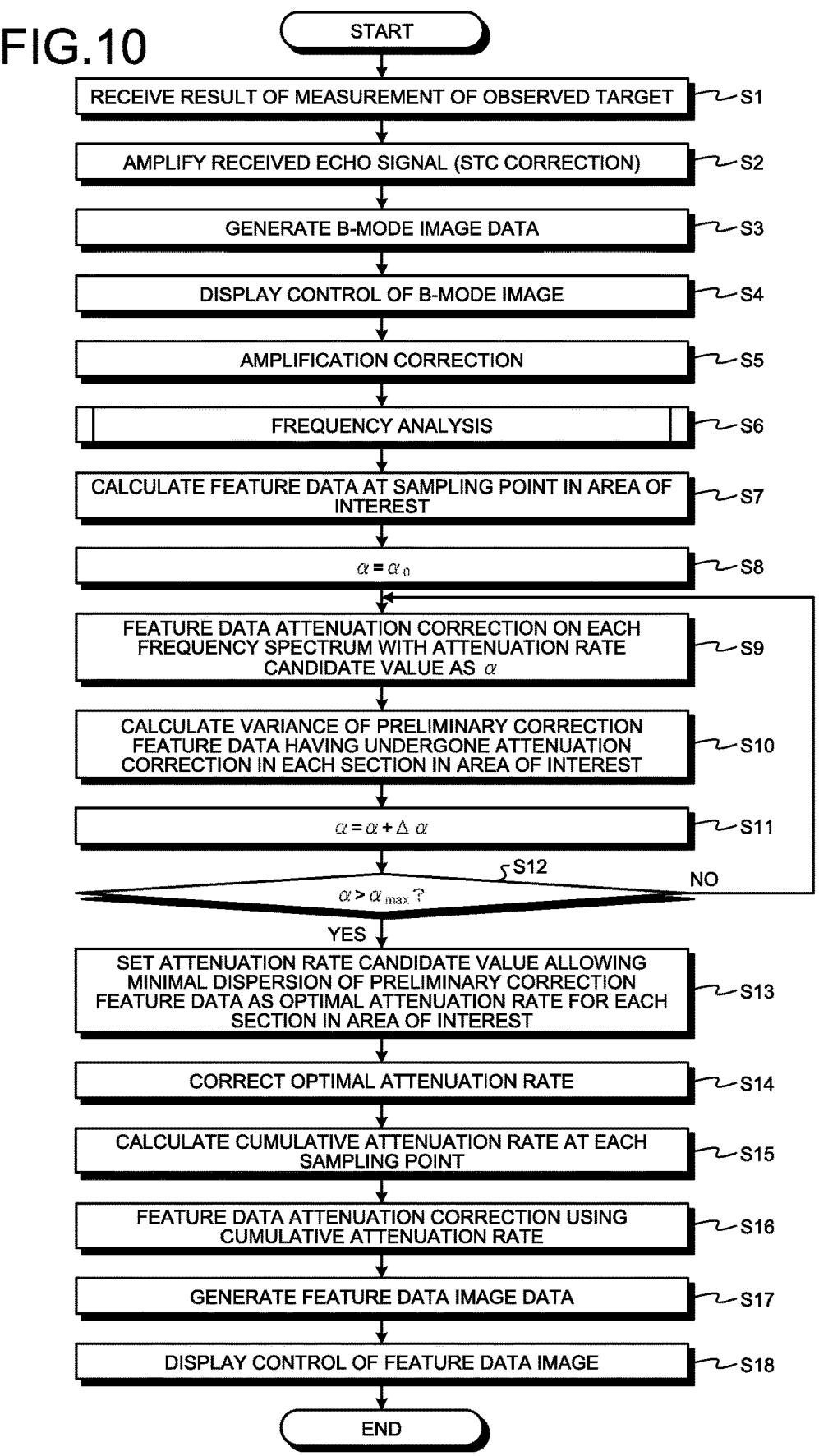
FIG. 10 is a flowchart that illustrates an overview of processing performed by the ultrasound observation device according to the first embodiment of the disclosure.

FIG. 10 is a flowchart that illustrates an overview of processing performed by the ultrasound observation device 3 having the above-described configuration. The flowchart in FIG. 10 illustrates processing performed with an area of interest on an ultrasound image already set after commencement of transmission of a transmission driving wave by the transmission and receipt unit 31 and commencement of transmission of ultrasound by the ultrasound transducer 21, in the ultrasound diagnosis system 1.

The ultrasound observation device 3 receives an echo signal as a result of measurement of an observed target by the ultrasound transducer 21 from the ultrasound endoscope 2 (Step S1).

The signal amplification unit 311 receives the echo signal from the ultrasound transducer 21 and amplifies the echo signal (Step S2). The signal amplification unit 311 amplifies (STC correction) the echo signal based on, for example, relation between the amplification rate and the receiving depth illustrated in FIG. 2.

The B-mode image data generating unit 341 generates B-mode image data using the echo signal amplified by the signal amplification unit 311 (Step S3). The display control unit 361 controls the display device 4 to display a B-mode image corresponding to the B-mode image data (Step S4).

The amplification correction unit 331 provides amplification correction on RF data output from the transmission and receipt unit 31 such that the amplification rate becomes constant regardless of the receiving depth (Step S5). The amplification correction unit 331 performs amplification correction, for example, based on relation between the amplification rate and the receiving depth illustrated in FIG. 3.

Figure 11:
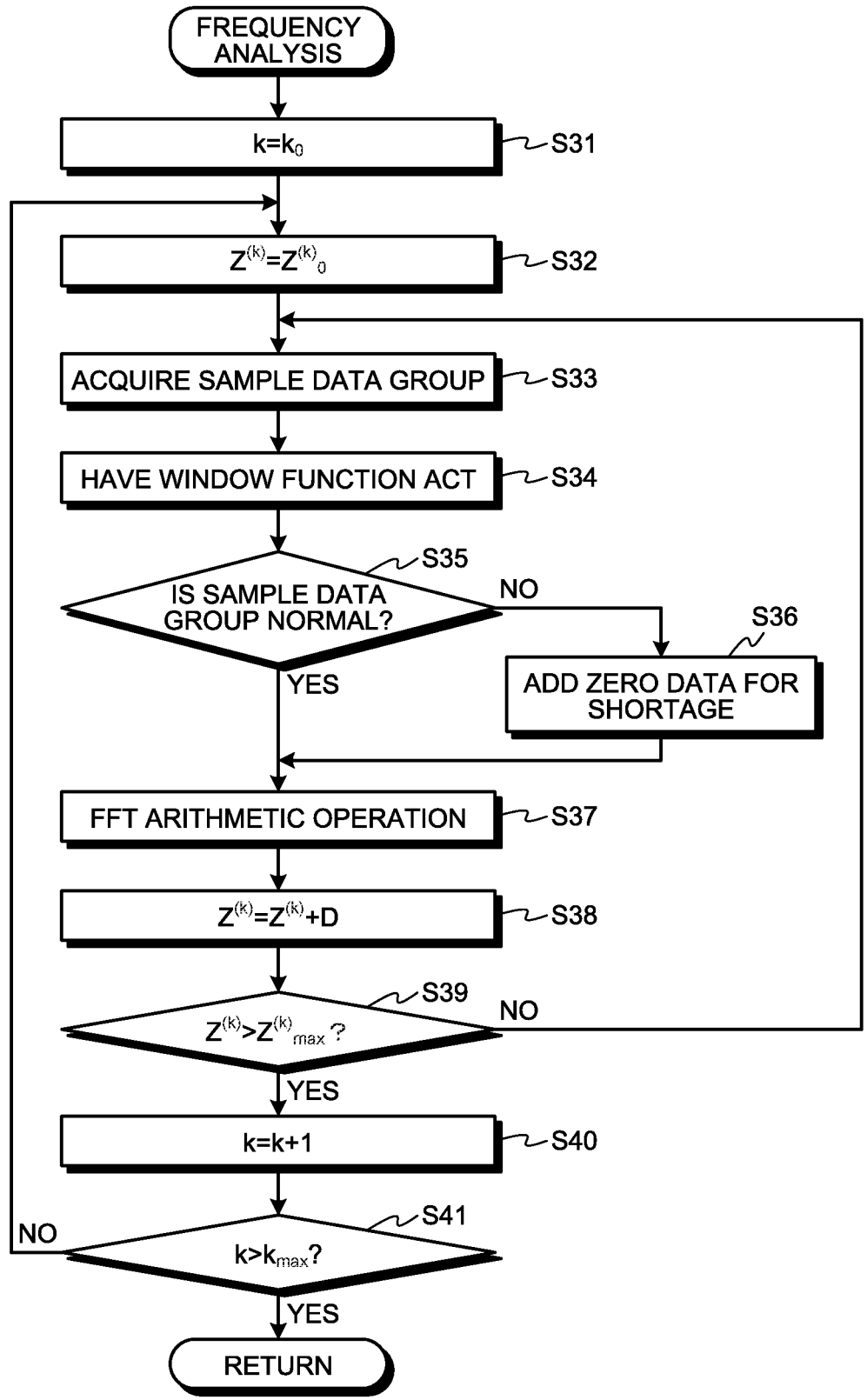
FIG. 11 is a flowchart that illustrates an overview of processing performed by the frequency analysis unit of the ultrasound observation device according to the first embodiment of the disclosure.

The frequency analysis unit 332 calculates a frequency spectrum corresponding to each sample data group by performing frequency analysis using the FFT on RF data of a sound ray after amplification correction and stores the spectrum in the spectrum information storage unit 372 (Step S6). FIG. 11 is a flowchart that illustrates an overview of processing performed by the frequency analysis unit 332 at Step S6. The frequency analysis processing will now be described in detail with reference to the flowchart illustrated in FIG. 11.

The frequency analysis unit 332 sets $k_0$ for a counter k for differentiating an analyzed sound ray (Step S31).

The frequency analysis unit 332 sets an initial value $Z^{(k)}_0$ of a data position (corresponding to the receiving depth) $Z^{(k)}$ representing a series of data groups (sample data groups) generated for FFT arithmetic operation (Step S32). For example, as described earlier, the eighth data position of the sound ray $SR_k$ is set as the initial value $Z^{(k)}_0$ in FIG. 4.

The frequency analysis unit 332 acquires a sample data group (Step S33) and has a window function stored in the storage unit 37 act on the acquired sample data group (Step S34). Action of the window function on a sample data group prevents the sample data group from being discontinuous at a boundary and prevents artifacts.

The frequency analysis unit 332 determines whether a sample data group having a data position $Z^{(k)}$ is a normal data group (Step S35). As described with reference to FIG. 4, a sample data group needs to include data pieces expressed in powers of two. The number of normal sample data groups will be expressed as $2^n$ (where n is an integer). In the first embodiment, the data position $Z^{(k)}$ is set in a manner situated as close to the center of a sample data group where $Z^{(k)}$ belongs to as possible. Specifically, the number of data pieces of the sample data group is $2^n$, and $Z^{(k)}$ is therefore set in the $2^n/2$ ($=2^{n-1}$)$^{th}$ position that is close to the center of the sample data group. In this case, normality of the sample data group indicates that the data group has $2^{n-1}-1$ (referred to as N) data pieces in the shallow side with respect to the data position $Z^{(k)}$ and has $2^{n-1}$ (referred to as M) data pieces in the deep side with respect to the data position $Z^{(k)}$. In FIG. 4, the sample data group $F_j$ (j=1, 2, ..., K-1) is therefore normal. In the example of FIG. 4, n=4 (N=7, M=8) is given.

If the sample data group having the data position $Z^{(k)}$ is determined to be normal (Yes at Step S35) as a result of determination at Step S35, the frequency analysis unit 332 proceeds to the later-described Step S37.

If the sample data group having the data position $Z^{(k)}$ is determined to be abnormal (No at Step S35) as a result of determination at Step S35, the frequency analysis unit 332 generates a normal sample data group by adding zero data for the shortage (Step S36). A window function acts on the sample data group (for example, the sample data group $F_K$ in FIG. 4) determined to be abnormal at Step S35 before addition of zero data. Discontinuity of data therefore does not occur even when zero data is added to the sample data group. After Step S36, the frequency analysis unit 332 proceeds to the later-described Step S37.

At Step S37, the frequency analysis unit 332 performs FFT arithmetic operation using the sample data group and acquires a frequency spectrum as a frequency distribution to the amplitude (Step S37).

The frequency analysis unit 332 changes the data position $Z^{(k)}$ at a step width D (Step S38). The step width D is preliminarily stored in the storage unit 37. In the example of FIG. 4, D=15 is given. The step width D preferably matches with the data step width used in generation of B-mode image data by the B-mode image data generating unit 341; however, a larger value than the data step width may be set for the step width D in trying to reduce the computational complexity in the frequency analysis unit 332.

The frequency analysis unit 332 determines whether the data position $Z^{(k)}$ is larger than a maximum value $Z^{(k)}_{max}$ of the sound ray $SR_k$ (Step S39). If the data position $Z^{(k)}$ is larger than the maximum value $Z^{(k)}_{max}$ (Yes at Step S39), the frequency analysis unit 332 increases the counter k by one (Step S40). The increase means that processing is moved to the next sound ray. On the other hand, if the data position $Z^{(k)}$ is equal to or smaller than the maximum value $Z^{(k)}_{max}$ (No at Step S39), the frequency analysis unit 332 returns to Step S33.

After Step S40, the frequency analysis unit 332 determines whether the counter k is larger than the maximum value $k_{max}$ (Step S41). If the counter k is larger than the maximum value $k_{max}$ (Yes at Step S41), the frequency analysis unit 332 ends this series of frequency analysis processing. If the counter k is equal to or smaller than the maximum value $k_{max}$ (No at Step S41), the frequency analysis unit 332 returns to Step S32. The maximum value $k_{max}$ is any value input according to an instruction from a user such as an operator through the input unit 35 or a value preliminarily set in the storage unit 37.

In this manner, the frequency analysis unit 332 provides a plurality of times of FFT arithmetic operation on each of ($k_{max}-k_0+1$) sound rays in an analyzed target area. Frequency spectra obtained from the FFT arithmetic operation are stored in the spectrum information storage unit 372 along with the receiving depth and the receiving direction.

In the above description, the frequency analysis unit 332 performs the frequency analysis processing on all the areas having received ultrasound signals. In another manner, the frequency analysis unit 332 may perform the frequency analysis processing only on an area of interest.

After the above-described frequency analysis processing at Step S6, the feature data calculation unit 333 calculates feature data of a frequency spectrum at a sampling point included in the area of interest (Step S7). More specifically, the feature data calculation unit 333 performs regression analysis on a frequency spectrum in a predetermined bandwidth and approximates the frequency spectrum with a linear formula $I=a_0 f+b_0$ and calculates the slope $a_0$, the intercept $b_0$, and the mid-band fit $c_0$ as feature data. For example, the straight line $L_{10}$ illustrated in FIG. 5 is a line of regression obtained with the feature data calculation unit 333 approximating the frequency spectrum $C_1$ in the bandwidth U using regression analysis.

The attenuation rate setting unit 334 sets an attenuation rate candidate value a used in the later-described attenuation correction as a predetermined initial value $\alpha_0$ (Step S8). The initial value $\alpha_0$ is preliminarily stored in the attenuation rate information storage unit 374. In another configuration, the input unit 35 may receive an input to change the setting of the initial value $\alpha_0$ of an attenuation rate candidate value.

The attenuation rate setting unit 334 performs attenuation correction on feature data obtained with the feature data calculation unit 333 approximating a frequency spectrum, using an attenuation rate candidate value $\alpha$ and calculates preliminary correction feature data and stores the calculated preliminary correction feature data in the feature data information storage unit 373 along with the attenuation rate candidate value $\alpha$ (Step S9). The straight line $L_1$ illustrated in FIG. 7 is an exemplary line obtained with the attenuation rate setting unit 334 performing the attenuation correction processing.

At Step S9, the attenuation rate setting unit 334 calculates the preliminary correction feature data by substituting the data position $Z=(f_{sp}/2v_s)$ Dn obtained based on the data array of a sound ray of an ultrasound signal to the receiving depth z in the above-described formulae (2) and (4). In the formula, $f_{sp}$ denotes a sampling frequency of data, $v_s$ denotes the speed of sound, D denotes a data step width, and n denotes the number of data steps from the first data on the sound ray to the data position in a sample data group as a processing target. For example, if the sampling frequency of data $f_{sp}$ is 50 MHz, the speed of sound $v_s$ is 1530 m/sec, and the data step width D is 15 by adapting the data array of FIG. 4, Z=0.2295n (mm) is given.

The attenuation rate setting unit 334 calculates variance of a preliminary correction feature data piece selected from a plurality of preliminary correction feature data pieces obtained with the attenuation rate setting unit 334 performing attenuation correction on frequency spectra and stores the variance in the feature data information storage unit 373 in a manner associated with the attenuation rate candidate value $\alpha$ (Step S10). For example, if the preliminary correction feature data pieces are the slope a and the mid-band fit c, the attenuation rate setting unit 334 calculates variance of either one of the preliminary correction feature data a and c as described above. As described above, if the feature data image data generating unit 342 generates feature data image data using the correction feature data $a_f(z)$ in the subsequent processing, variance of the preliminary correction feature data a in the area of interest is preferably used. If the feature data image data generating unit 342 generates feature data image data using the correction feature data $c_f(z)$ in the subsequent processing, variance of the preliminary correction feature data c in the area of interest is preferably used. Preliminary correction feature data used for calculation of variance may be preliminarily set, or a user may set the preliminary correction feature data by inputting an instruction signal instructing desired preliminary correction feature data through the input unit 35.

The attenuation rate setting unit 334 increases a value of the attenuation rate candidate value $\alpha$ by $\Delta\alpha$ (Step S11) and compares the value magnitude between the increased attenuation rate candidate value $\alpha$ and a predetermined maximum value $\alpha_{max}$ (Step S12). If the attenuation rate candidate value $\alpha$ is found to be larger than the maximum value $\alpha_{max}$ (Yes at Step S12) from a result of comparison at Step S12, the ultrasound observation device 3 proceeds to Step S13. If the attenuation rate candidate value $\alpha$ is found to be equal to or smaller than the maximum value $\alpha_{max}$ (No at Step S12) from a result of comparison at Step S12, the ultrasound observation device 3 returns to Step S9. In another configuration, the input unit 35 may receive an input to change the setting of the amount of increase $\Delta\alpha$ in the attenuation rate candidate value and the maximum value $\alpha_{max}$.

At Step S13, the attenuation rate setting unit 334 refers to variance of preliminary correction feature data for each attenuation rate candidate value stored in the feature data information storage unit 373 and sets an attenuation rate candidate value allowing the minimal variance as an optimal attenuation rate, for the area of interest (Step S13).

Figure 12:
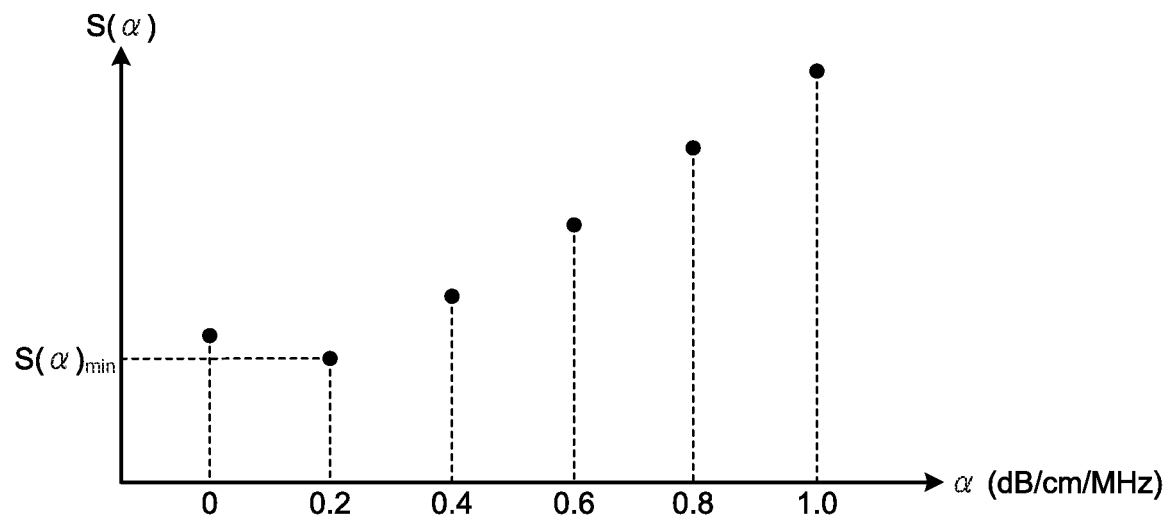
FIG. 12 is a drawing that illustrates an overview of processing performed by the attenuation rate setting unit of the ultrasound observation device according to the first embodiment of the disclosure.

FIG. 12 is a drawing that illustrates an overview of processing performed by the attenuation rate setting unit 334. FIG. 12 is a drawing that illustrates exemplary relation between the attenuation rate candidate value $\alpha$ and variance $S(\alpha)$ where $\alpha_0=0$ (dB/cm/MHz), $\alpha_{max}=1.0$ (dB/cm/MHz), and $\Delta\alpha=0.2$ (dB/cm/MHz) are given. In the example of FIG. 12, variance takes a minimum value $S(\alpha)_{min}$ when an attenuation rate candidate value $\alpha$ is 0.2 (dB/cm/MHz). In the example of FIG. 12, the attenuation rate setting unit 334 therefore sets $\alpha=0.2$ (dB/cm/MHz) as an optimal attenuation rate. After the feature data calculation unit 333 calculates a curved line interpolating values of variance $S(\alpha)$ for the attenuation rate candidate value $\alpha$ using regression analysis, the attenuation rate setting unit 334 may set the minimum value on the curved line in a definition range of the attenuation rate candidate value as an optimal attenuation rate.

The attenuation rate correction unit 335 performs correction such that the optimal attenuation rate smoothly changes across adjacent sections (Step S14). As described with reference to FIG. 9, the attenuation rate correction unit 335 linearly interpolates optimal attenuation rates $\alpha_f(z)$ determined for respective sections $P_1$ using straight lines.

The feature data correction unit 336 calculates a cumulative attenuation rate at a sampling point in the area of interest using the optimal attenuation rates set by the attenuation rate setting unit 334 (Step S15). For example, the cumulative attenuation rate $\gamma_2(z)$ at a sampling point $SP_2(z)$ in an area of interest 102 illustrated in FIG. 6 is calculated by giving I=2 for the formula (7).

The feature data correction unit 336 calculates correction feature data by providing attenuation correction on feature data at a sampling point in the area of interest using the cumulative attenuation rate (Step S16). For example, the feature data correction unit 336 calculates correction feature data $a_2(z)$, $b_2(z)$, and $c_2(z)$ of the slope $a_0$, the intercept $b_0$, and the mid-band fit $c_0$, respectively, at a sampling point $S(z)$ inside the area of interest 102 illustrated in FIG. 6 using the formulae (8) to (10).

The feature data image data generating unit 342 generates feature data image data by overlapping visual information (for example, hue) associated with the correction feature data calculated at Step S16 on each pixel in the area of interest on the B-mode image data generated by the B-mode image data generating unit 341 (Step S17). The display control unit 361 controls the display device 4 to display a feature data image corresponding to the generated feature data image data (Step S18).

After Step S18, the ultrasound observation device 3 ends this series of processing. The ultrasound observation device 3 periodically repeats the processing of Steps S1 to S18.

According to the above-described first embodiment, an attenuation rate in a range including at least a boundary between adjacent sections is corrected in a manner smoothly changing across the adjacent sections, and correction feature data is calculated by providing attenuation correction on feature data using the corrected attenuation rate. With this configuration, correction feature data can be calculated considering non-uniformity in the attenuation rate of an observed target. According to the first embodiment, tissue characteristics of an observed target having a non-uniform attenuation rate can be accurately identified.

According to the first embodiment, an attenuation rate is corrected in a manner smoothly changing across adjacent sections, which can prevent a sharp change in the attenuation rate on the boundary of the adjacent sections. Consequently, this configuration reduces unnecessary variations in brightness, which is likely to occur at the boundary between sections, and is therefore able to generate a feature data image allowing more accurate and more natural representation of tissue characteristics.

In the first embodiment, the attenuation rate correction unit 335 corrects an attenuation rate along the depth direction. Instead of this configuration, the attenuation rate correction unit 335 may correct an attenuation rate along the scan direction of the ultrasound transducer 21 or along both the depth direction and the scan direction.

In the first embodiment, a feature data image of an area of interest as a part of the full screen is generated. Instead of this manner, a feature data image having the whole area of an ultrasound image as an area of interest can be generated. In this case, correction feature data for the whole area of the ultrasound image may be calculated.

Modification

Figure 13:
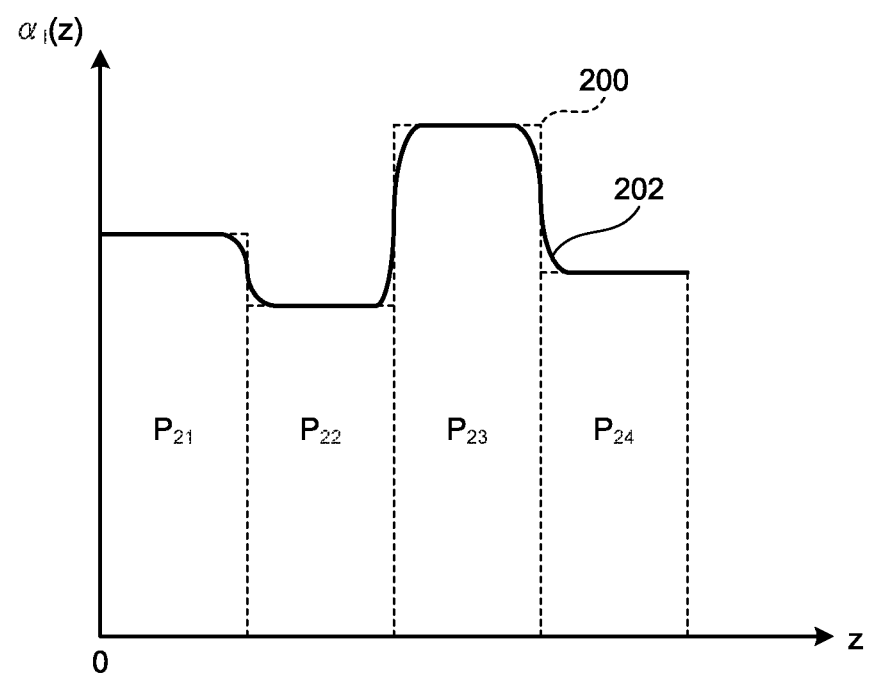
FIG. 13 is a drawing that illustrates an overview of correction processing performed by the attenuation rate correction unit of the ultrasound observation device according to a modification of the first embodiment of the disclosure.

FIG. 13 is a drawing that illustrates an overview of correction processing performed by the attenuation rate correction unit 335 of the ultrasound observation device 3 according to a modification of the first embodiment. In a first modification, the attenuation rate correction unit 335 includes a filter (a spatial filter) for performing processing for having nearby area of a boundary between sections smoothly change along the depth direction. A curved line 202 illustrated in FIG. 13 is obtained with the attenuation rate correction unit 335 providing correction processing on the histogram 200. It should be noted that this modification exerts the same advantageous effects as those of the first embodiment.

Second Embodiment

A second embodiment of the disclosure has a step of smoothing feature data calculated by a feature data calculation unit as pre-processing for calculating optimal feature data in each section of an area of interest.

Figure 14:
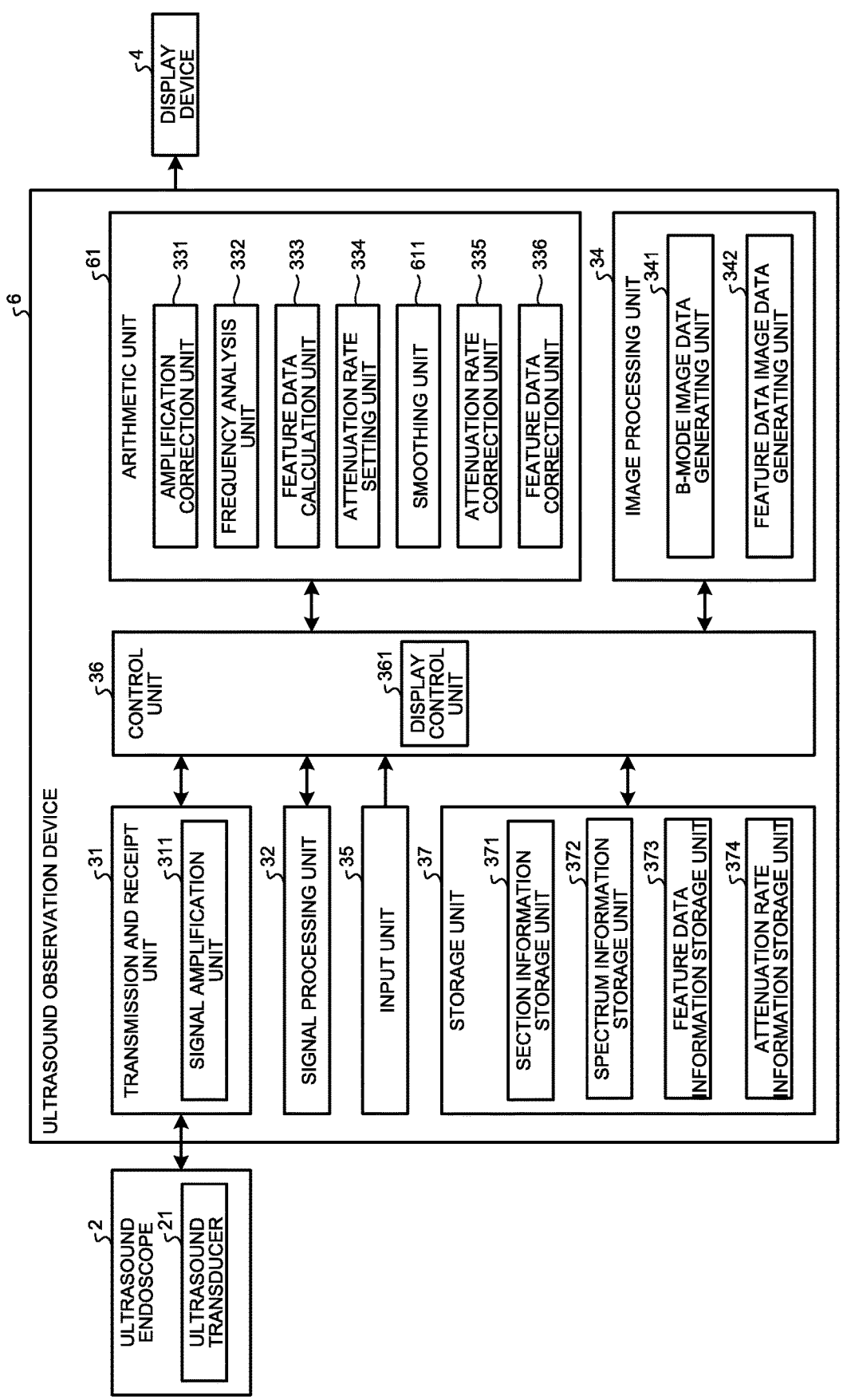
FIG. 14 is a block diagram that illustrates a functional configuration of an ultrasound diagnosis system having an ultrasound observation device according to a second embodiment of the disclosure.

FIG. 14 is a block diagram that illustrates a functional configuration of an ultrasound diagnosis system having an ultrasound observation device according to the second embodiment of the disclosure. An ultrasound diagnosis system 5 illustrated in FIG. 14 has the ultrasound endoscope 2, and ultrasound observation device 6, and the display device 4. Like numerals are assigned to like components of the ultrasound diagnosis system 1 described in the first embodiment.

The ultrasound observation device 6 is different from the above-described ultrasound observation device 3 in the functional configuration of an arithmetic unit. More specifically, an arithmetic unit 61 included in the ultrasound observation device 6 has a smoothing unit 611 other than the amplification correction unit 331, the frequency analysis unit 332, the feature data calculation unit 333, the attenuation rate setting unit 334, the attenuation rate correction unit 335, and the feature data correction unit 336.

Figure 15:
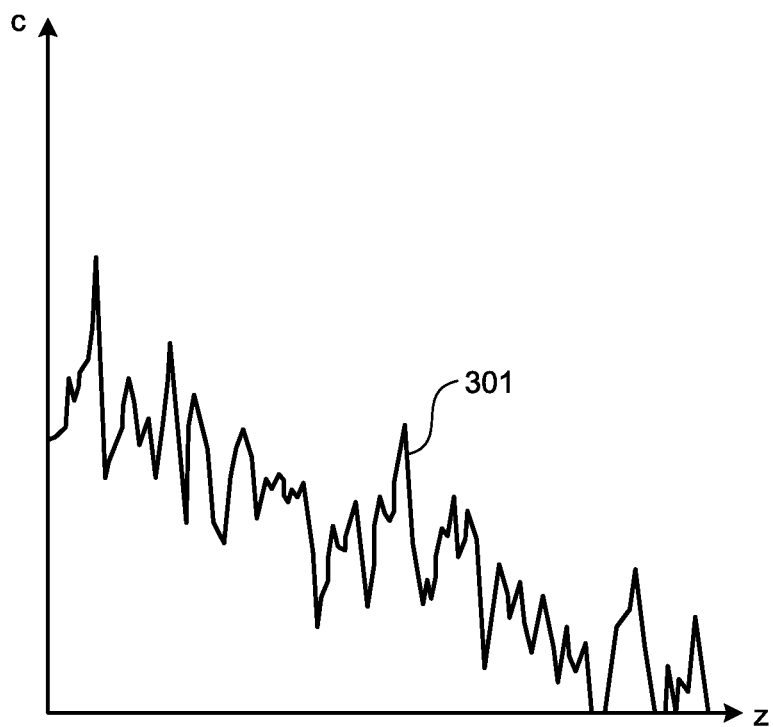
FIG. 15 is a drawing that illustrates exemplary feature data (feature data before smoothing) calculated by a feature data calculation unit of the ultrasound observation device according to the second embodiment of the disclosure.
Figure 16:
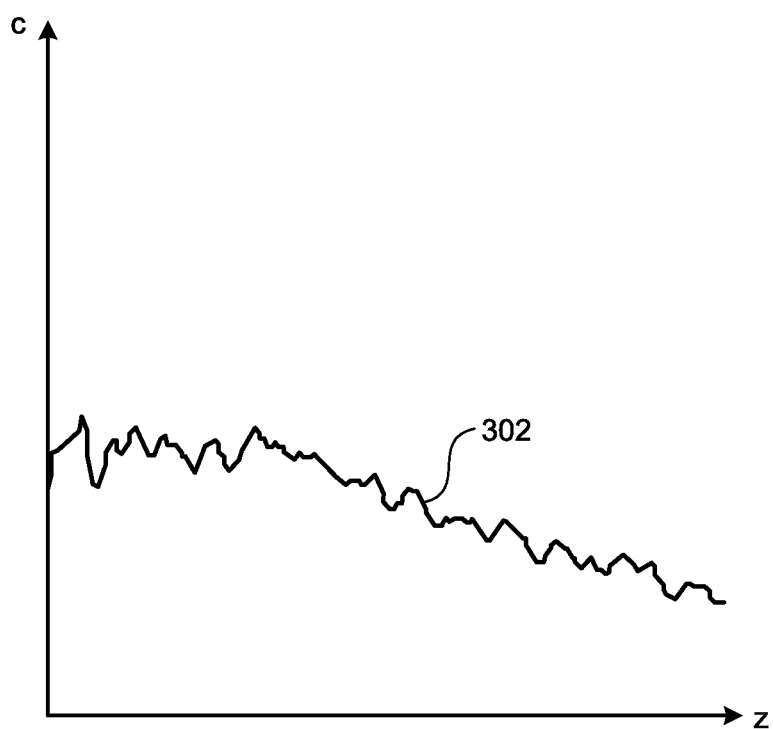
FIG. 16 is a drawing that illustrates exemplary feature data having undergone smoothing processing by a smoothing unit of the ultrasound observation device according to the second embodiment of the disclosure.

The smoothing unit 611 provides smoothing processing on feature data calculated by the feature data calculation unit 333. FIG. 15 is a drawing that illustrates exemplary feature data before smoothing calculated by the feature data calculation unit 333. FIG. 16 is a drawing that illustrates feature data obtained with the smoothing unit 611 providing smoothing processing on feature data illustrated in FIG. 15. A curved line 301 illustrated in FIG. 15 indicates relation between the mid-band fit c and the receiving depth z. The curved line 301 indicates a trend of a decrease in the mid-band fic c with an increase in the receiving depth z; however, the curved line 301 locally has marked fluctuations. On the other hand, fluctuations on a curved line 302 of FIG. 16 are mild compared to the curved line 301 although the curved line 302 indicates a like trend of a decrease in the mid-band fic c with an increase in the receiving depth z.

Figure 17:
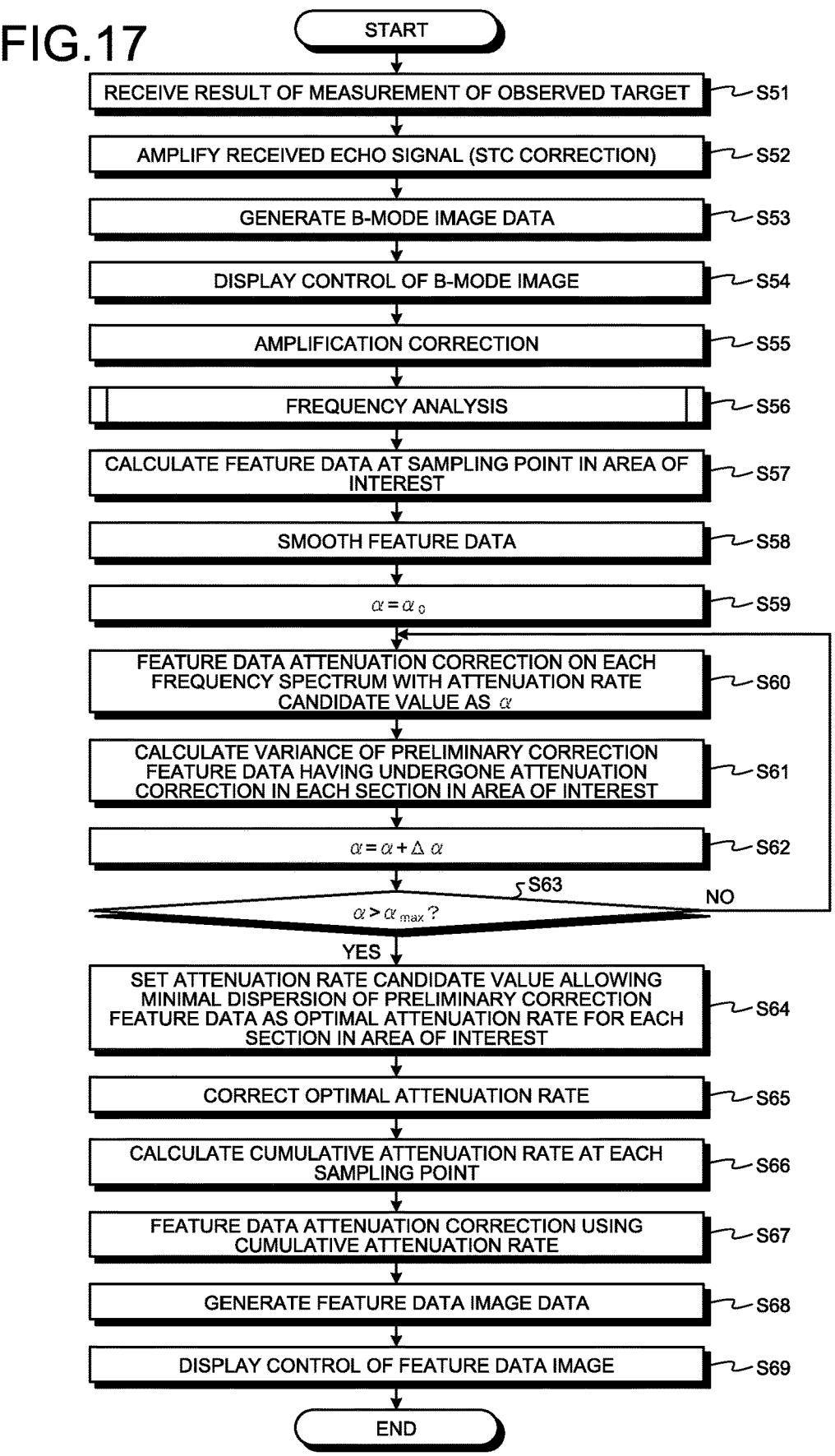
FIG. 17 is a flowchart that illustrates an overview of processing performed by the ultrasound observation device according to the second embodiment of the disclosure.

FIG. 17 is a flowchart that illustrates an overview of processing performed by the ultrasound observation device 6. The processing of Steps S51 to S57 corresponds to the processing of Steps S1 to S7 illustrated in FIG. 10, respectively in this order.

At Step S58 subsequent to Step S57, the smoothing unit 611 smooths feature data (Step S58). For example, the smoothing unit 611 obtains the curved line 302 of FIG. 16 by smoothing the curved line 301 of FIG. 15.

The processing of subsequent steps of S59 to S69 correspond to the processing of Steps S8 to S18 of FIG. 10, respectively in this order.

According to the above-described second embodiment of the disclosure, as is the case with the first embodiment, tissue characteristics of an observed target having a non-uniform attenuation rate can be accurately identified. Furthermore, unnecessary variations in brightness, which are likely to occur at the boundary between sections, can be reduced, and a feature data image allowing more accurate and more natural representation of the tissue characteristics can be therefore generated.

According to the second embodiment, feature data is smoothed along the depth direction before setting an optimal attenuation rate for each section. This process can reduce the variation in feature data in the depth direction that is one of factors of noise likely to be caused in setting an optimal attenuation rate.

As smoothing processing performed by the smoothing unit 611, results of calculation by the feature data calculation unit 333 may be linearly approximated using regression analysis.

Other Embodiments

Embodiments of the disclosure have been described as above; however, it should be noted that the disclosure is not limited to the above-described first and second embodiments. For example, a brightness value of an ultrasound image may be used as feature data. In this case, an optimal attenuation rate is set for each section based on a brightness value. After correction of the optimal attenuation rate, a brightness value serving as correction feature data is calculated using the corrected optimal attenuation rate.

The attenuation rate setting unit 334 may calculate an optimal attenuation rate corresponding value corresponding to an optimal attenuation rate for each frame of an ultrasound image and may set the average, the median, or the mode of a predetermined number of optimal attenuation rate corresponding values including an optimal attenuation rate corresponding value for the newest frame as an optimal attenuation rate. This method can reduce the variation in the optimal attenuation rate and make the value stable compared to a method setting an optimal attenuation rate for each frame.

The attenuation rate setting unit 334 may set optimal attenuation rates at predetermined frame intervals of an ultrasound image. This method allows a marked reduction in computational complexity. In this method, the optimal attenuation rate last set may be used until the next optimal attenuation rate is set.

In another configuration, the input unit 35 may receive an input to change setting of an initial value $\alpha_0$ of an attenuation rate candidate value.

For example, any one of the standard deviation, a difference between the maximum value and the minimum value of feature data in a population, and full width at half maximum of a distribution of feature data is usable as a measure of statistical dispersion. In another manner, the reciprocal of variance may be used as a measure of statistical dispersion. In this case, an attenuation rate candidate value making the value maximum corresponds to the optimal attenuation rate.

In still another manner, the attenuation rate setting unit 334 may calculate statistical dispersion of a plurality of types of preliminary correction feature data and set an attenuation rate candidate value deriving the minimal statistical dispersion as the optimal attenuation rate.

Furthermore, the attenuation rate setting unit 334 may calculate preliminary correction feature data by providing attenuation correction on a frequency spectrum using a plurality of attenuation rate candidate values and providing regression analysis on the frequency spectrum having undergone the attenuation correction.

The configuration is further applicable to an ultrasound probe other than an ultrasound endoscope. Examples of the ultrasound probe may include a small-diameter ultrasound miniature probe without optical systems. Such an ultrasound miniature probe is usually inserted to the biliary tract, the bile ducts, the pancreatic duct, the trachea, the bronchi, the urethra, and the ureters and is used for observation of the surrounding organs (such as the pancreas, the lungs, the prostate, the bladder, and the lymph nodes). An external ultrasound probe radiating ultrasound from the body surface of a subject may be used as an ultrasound probe. An external ultrasound probe is usually used for observation of abdominal organs (such as the liver, the gallbladder, and the bladder), the breasts (particularly, the mammary glands), and the thyroid gland.

Note

Figure 18:
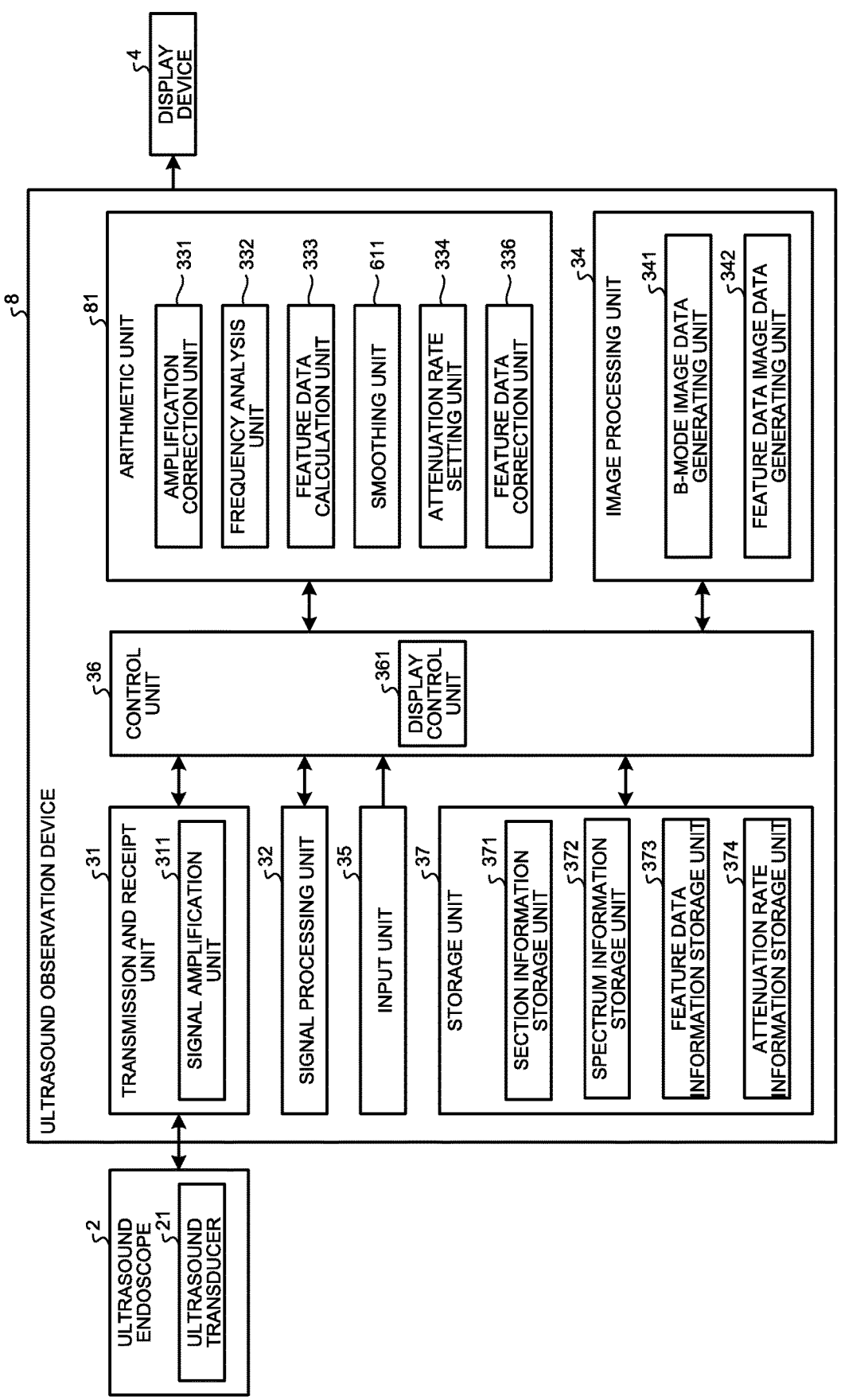
FIG. 18 is a block diagram that illustrates a functional configuration of an ultrasound diagnosis system having an ultrasound observation device according to a different embodiment.

FIG. 18 is a block diagram that illustrates a functional configuration of an ultrasound diagnosis system having an ultrasound observation device according to a different embodiment. An ultrasound diagnosis system 7 illustrated in FIG. 18 has the ultrasound endoscope 2, an ultrasound observation device 8, and the display device 4. Like numerals are assigned to like components of the ultrasound diagnosis system 1 described in the first embodiment.

The ultrasound observation device 8 includes the transmission and receipt unit 31, the signal processing unit 32, an arithmetic unit 81, the image processing unit 34, the input unit 35, the control unit 36, and the storage unit 37. The arithmetic unit 81 has the amplification correction unit 331, the frequency analysis unit 332, the feature data calculation unit 333, the smoothing unit 611, the attenuation rate setting unit 334, and the feature data correction unit 336.

Figure 19:
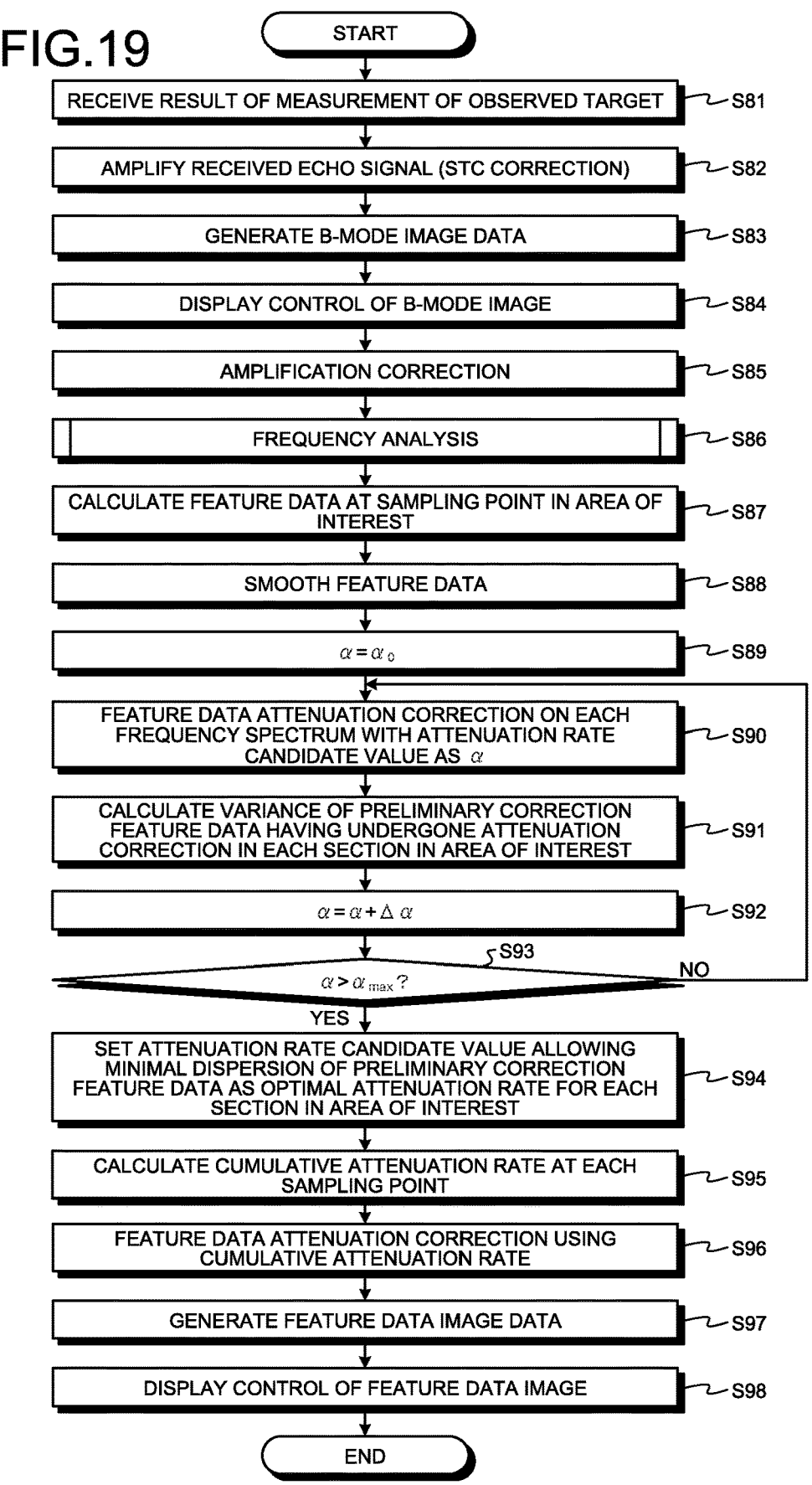
FIG. 19 is a flowchart that illustrates an overview of processing performed by the ultrasound observation device according to the different embodiment.

FIG. 19 is a flowchart that illustrates an overview of processing performed by the ultrasound observation device 8. The processing of Steps S81 to S94 corresponds to the processing of Steps S51 to S64 illustrated in FIG. 17, respectively in this order.

In the different embodiment, after Step S94, the feature data correction unit 336 calculates a cumulative attenuation rate at a sampling point in an area of interest using an optimal attenuation rate set by the attenuation rate setting unit 334 (Step S95). The processing of Step S95 is the same as the processing of Step S15 of FIG. 10 in the first embodiment.

The processing of subsequent steps of S96 to S98 correspond to the processing of Steps S16 to S18 of FIG. 10 in the first embodiment, respectively in this order.

After Step S98, the ultrasound observation device 8 ends this series of processing. The ultrasound observation device 8 periodically repeats the processing of Steps S81 to S98.

According to the different embodiment, feature data is smoothed along the depth direction before setting of an optimal attenuation rate for each section. This process can reduce the variation in feature data in the depth direction that is one of factors of noise likely to be caused in setting an optimal attenuation rate.

In the different embodiment, the smoothing unit 611 may linearly approximate results of calculation by the feature data calculation unit 333 using regression analysis. In the different embodiment, an optimal attenuation rate may be calculated for an area of interest, which is not divided. In the different embodiment, configurations and others in the earlier-described other embodiments may be implemented in combination as appropriate.

Note 1

An ultrasound observation device configured to generate an ultrasound image based on an ultrasound signal acquired by an ultrasound probe including an ultrasound transducer that transmits ultrasound to an observed target and receives ultrasound reflected on the observed target, the ultrasound observation device including:

a feature data calculation unit configured to calculate feature data of the ultrasound signal by analyzing the ultrasound signal;

a smoothing unit configured to smooth the feature data calculated by the feature data calculation unit along a receiving depth of the ultrasound;

an attenuation rate setting unit configured to set an attenuation rate giving attenuation characteristics to the ultrasound propagating through the observed target based on the feature data smoothed by the smoothing unit; and a feature data correction unit configured to perform attenuation correction on the feature data using an attenuation rate set by the attenuation rate setting unit to calculate correction feature data.

According to some embodiments, tissue characteristics of an observed target with a non-uniform attenuation rate can be accurately identified.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation device comprising:
a controller, wherein the controller is configured to:
calculate feature data of an ultrasound signal by analyzing the ultrasound signal;
divide an area of interest preliminarily set on an ultrasound image into a plurality of sections; and
set an attenuation rate for each of the sections;
correct the attenuation rate in a range including at least a boundary between adjacent sections in a manner smoothly changing across the adjacent sections; and
perform attenuation correction on the feature data using the corrected attenuation rate to calculate correction feature data;
wherein the calculation of the feature data comprises:
analyzing a frequency of the ultrasound signal to calculate a plurality of frequency spectra corresponding to a receiving depth and a receiving direction of the ultrasound signal; and
calculating feature data of each of the frequency spectra.

2. The ultrasound observation device according to claim 1, wherein the controller is configured to interpolate the attenuation rate in the range including the boundary between the adjacent sections using a straight line or a curved line.

3. The ultrasound observation device according to claim 1, wherein the controller includes a filter for smoothing the range including the boundary between the adjacent sections.

4. The ultrasound observation device according to claim 1, wherein the controller is further configured to:
smooth the calculated feature data along the receiving depth of the ultrasound; and
set the attenuation rate based on the smoothed feature data.

5. The ultrasound observation device according to claim 1, wherein the controller is configured to:
in each of the sections, perform attenuation correction for removing an effect of the ultrasound on feature data of each frequency spectrum using a plurality of attenuation rate candidate values per unit length and per unit frequency giving respective different attenuation characteristics to the ultrasound propagating through the observed target to calculate preliminary correction feature data of the frequency spectrum for each of the attenuation rate candidate values;
set an optimal attenuation rate for the observed target among the attenuation rate candidate values based on a result of the calculation;
correct the optimal attenuation rate in a manner smoothly changing across adjacent sections along a depth direction of the ultrasound signal;
calculate a cumulative attenuation rate per unit frequency at a sampling point using an optimal attenuation rate of a section situated between a surface of the ultrasound transducer and the sampling point among corrected optimal attenuation rates of the respective sections; and
perform attenuation correction on the feature data using the cumulative attenuation rate to calculate correction feature data.

6. The ultrasound observation device according to claim 5, wherein the controller is configured to calculate statistical dispersion of the preliminary correction feature data for each of the attenuation rate candidate values and determine an attenuation rate candidate value allowing minimal statistical dispersion to be the optimal attenuation rate.

7. The ultrasound observation device according to claim 1, wherein the controller is configured to calculate brightness of the ultrasound image as the feature data.

8. The ultrasound observation device according to claim 5, wherein the controller is configured to:
   approximate a predetermined bandwidth of the frequency spectrum using a linear formula;
   calculate any one or some of an intercept of the linear formula, a slope of the linear formula, and a mid-band fit as the feature data, the mid-band fit being a value of the linear formula on an intermediate frequency of the bandwidth, the calculated feature data including either one of the slope and the mid-band fit; and
   set the optimal attenuation rate based on either one of the slope and the mid-band fit.

9. The ultrasound observation device according to claim 8, wherein the controller is configured to set the optimal attenuation rate based on the slope when the slope is used as the feature data and set the optimal attenuation rate based on the mid-band fit when the mid-band fit is used as the feature data.

10. The ultrasound observation device according to claim 1, wherein the controller is further configured to generate feature data image data displaying information about the correction feature data together with the ultrasound image.

11. A method of operating an ultrasound observation device, the method comprising:
   calculating, by a controller, feature data of an ultrasound signal by analyzing the ultrasound signal;
   dividing, by the controller, an area of interest preliminarily set on an ultrasound image into a plurality of sections and setting an attenuation rate for each of the sections;
   correcting, by the controller, the attenuation rate in a range including at least a boundary between adjacent sections in a manner smoothly changing across the adjacent sections; and
   performing, by the controller, attenuation correction on the feature data using the corrected attenuation rate to calculate correction feature data;
   wherein the calculating of the feature data comprises:
      analyzing a frequency of the ultrasound signal to calculate a plurality of frequency spectra corresponding to a receiving depth and a receiving direction of the ultrasound signal; and
      calculating feature data of each of the frequency spectra.

12. The method according to claim 11, wherein the correcting of the attenuation rate includes interpolating the attenuation rate in the range including the boundary between the adjacent sections using a straight line or a curved line.

13. The method according to claim 11, wherein the correcting of the attenuation rate includes correcting the attenuation rate in the range including the boundary between the adjacent sections using a filter for smoothing the range including the boundary between the adjacent sections.

14. A non-transitory computer-readable recording medium with an executable program stored thereon, the program operating an ultrasound observation device, the program causing the ultrasound observation device to execute:
   calculating, by a controller, feature data of an ultrasound signal by analyzing the ultrasound signal;
   dividing, by the controller, an area of interest preliminarily set on an ultrasound image into a plurality of sections and setting an attenuation rate for each of the sections;
   correcting, by the controller, the attenuation rate in a range including at least a boundary between adjacent sections in a manner smoothly changing across the adjacent sections; and
   performing, by the controller, attenuation correction on the feature data using the corrected attenuation rate to calculate correction feature data;
   wherein the calculating of the feature data comprises:
      analyzing a frequency of the ultrasound signal to calculate a plurality of frequency spectra corresponding to a receiving depth and a receiving direction of the ultrasound signal; and
      calculating feature data of each of the frequency spectra.

15. The non-transitory computer-readable recording medium according to claim 14, wherein the correcting of the attenuation rate includes interpolating the attenuation rate in the range including the boundary between the adjacent sections using a straight line or a curved line.

16. The non-transitory computer-readable recording medium according to claim 14, wherein the correcting of the attenuation rate includes correcting the attenuation rate in the range including the boundary between the adjacent sections using a filter for smoothing the range including the boundary between the adjacent sections.

* * * * *